US012667611B2

(12) United States Patent
Kalergis et al.

(10) Patent No.: US 12,667,611 B2
(45) Date of Patent: Jun. 30, 2026

(54) USE OF BCG IMMUNOGENIC FORMULATION EXPRESSING A RESPIRATORY SYNCITIAL VIRUS PROTEIN AGAINST HMPV

(71) Applicant: PONTIFICIA UNIVERSIDAD CATOLICA DE CHILE, Santiago (CL)

(72) Inventors: Alexis Kalergis, Santiago (CL); Susan Bueno, Santiago (CL); Pablo González, Santiago (CL)

(73) Assignee: Pontificia Universidad Catolica de Chile, Santiago (CL)

( * ) Notice: Subject to any disclaimer, the term of this patent is extended or adjusted under 35 U.S.C. 154(b) by 227 days.

(21) Appl. No.: 17/757,972

(22) PCT Filed: Dec. 24, 2020

(86) PCT No.: PCT/CL2020/050193
§ 371 (c)(1),
(2) Date: Jun. 24, 2022

(87) PCT Pub. No.: WO2021/127797
PCT Pub. Date: Jul. 1, 2021

(65) Prior Publication Data
US 2023/0055706 A1 Feb. 23, 2023

(30) Foreign Application Priority Data

Dec. 26, 2019 (CL) .................................. 3847-2019

(51) Int. Cl.
| | |
|---|---|
| *A61K 39/04* | (2006.01) |
| *A61K 39/00* | (2006.01) |
| *A61K 39/12* | (2006.01) |
| *A61P 31/14* | (2006.01) |

(52) U.S. Cl.
CPC .............. *A61K 39/12* (2013.01); *A61P 31/14* (2018.01); *A61K 2039/523* (2013.01); *C12N 2760/18534* (2013.01)

(58) Field of Classification Search
None
See application file for complete search history.

(56) References Cited

U.S. PATENT DOCUMENTS 8,398,993 B2    3/2013  Kalergis Parra et al.
9,999,663 B2 *  6/2018  Bueno Ramirez ....... C12N 7/00

FOREIGN PATENT DOCUMENTS

EP        3 054 013         8/2016
WO      WO 2015049633 A1 *  4/2015

OTHER PUBLICATIONS

English translation of WO 2015049633 A1, pp. 1-22, 2015.*
International Search Report issued in International Application No. PCT/CL2020/050193, Apr. 1, 2021, 6 pages w/translation.
Zhang, et al., "Serologic cross-reactions between nucleocapsid proteins of human respiratory syncytial virus and human metapneumovirus", J Clin Microbiol., 53:5, May 2015, pp. 1609-1615.
Covian, et al., "BCG_Induced Cross-Protection and Development of Trained Immunity: Implication for Vaccine Design", Frontiers in Immunology, vol. 10, article 2806, Nov. 29, 2019, 14 pages.

* cited by examiner

*Primary Examiner* — S. Devi
(74) *Attorney, Agent, or Firm* — HSML P.C.

(57) ABSTRACT

The invention relates to the novel use of an immunogenic formulation containing the *bacillus* Calmette-Guérin (BCG) strain at a concentration between 10-10° bacteria, expressing at least one protein or immunogenic fragment of respiratory syncytial virus (RSV, Human *Orthopneumovirus*), in a pharmaceutically acceptable saline buffer solution because it serves to prepare a vaccine useful to prevent, treat, or attenuate human *Metapneumovirus* (hMPV) infections.

9 Claims, 8 Drawing Sheets

Specification includes a Sequence Listing.

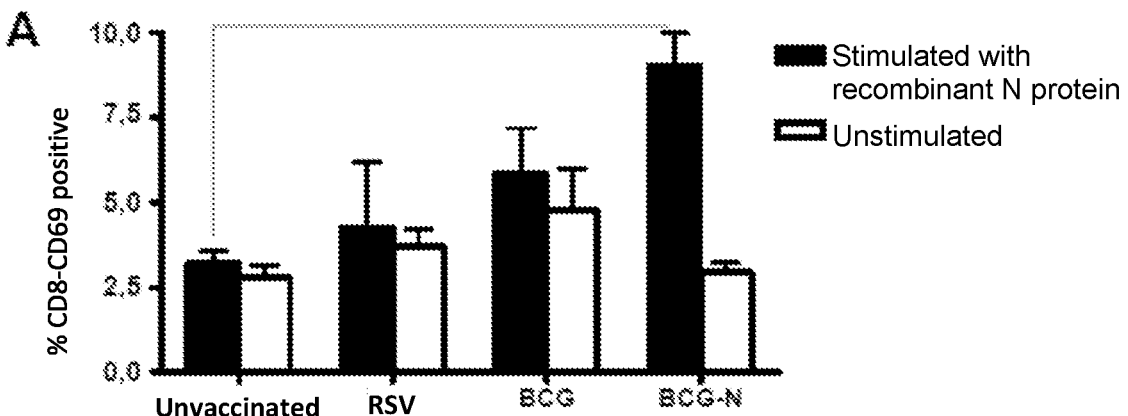
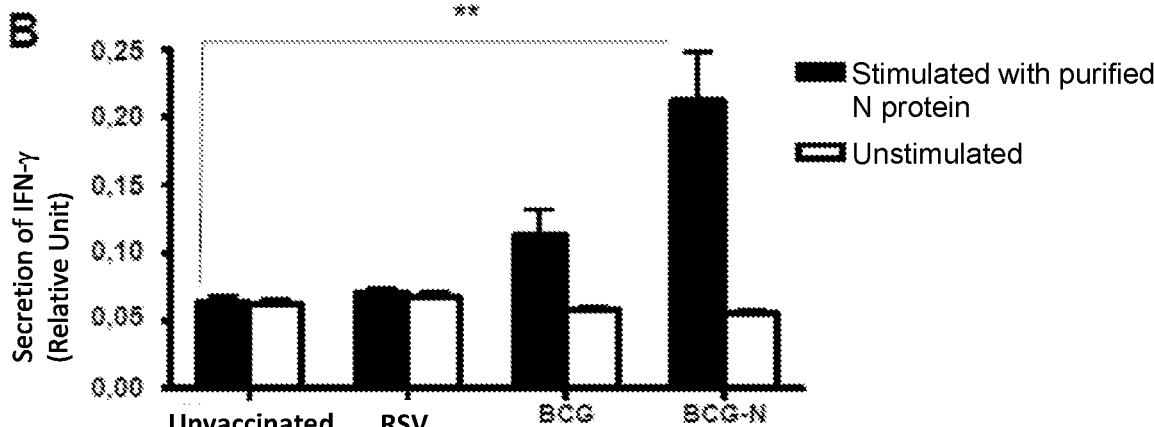
Fig. 1

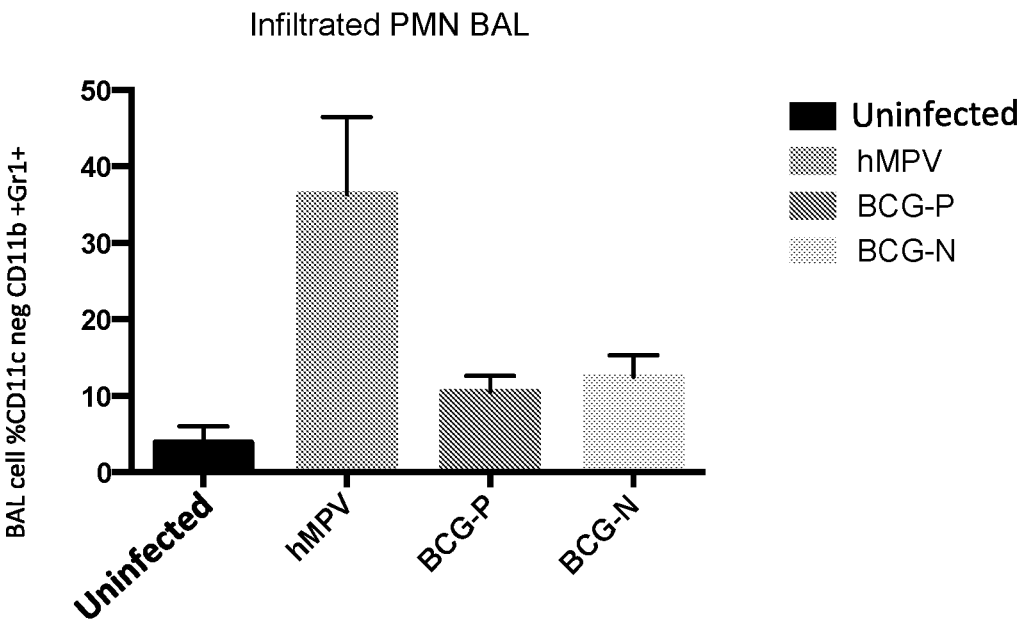
Fig. 3-A
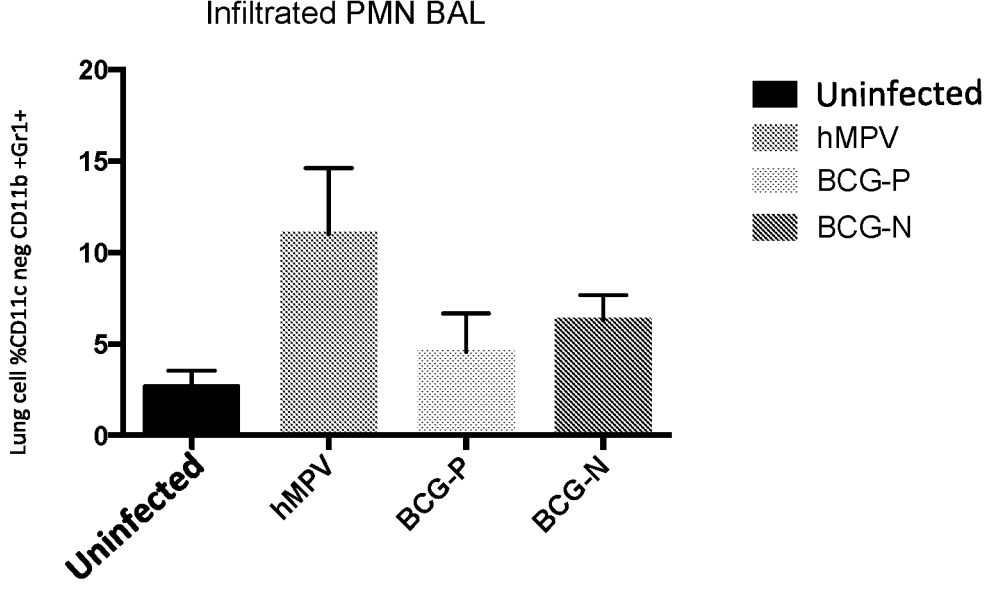
Fig. 3-B

USE OF BCG IMMUNOGENIC FORMULATION EXPRESSING A RESPIRATORY SYNCITIAL VIRUS PROTEIN AGAINST HMPV

FIELD OF THE INVENTION

An immunogenic formulation useful for preparing a vaccine against respiratory viruses, such as respiratory syncytial virus (RSV, Human *Orthopneumovirus*) and/or human *Metapneumovirus* (hMPV), is disclosed, where this formulation comprises at least one attenuated strain of *Mycobacterium*, preferably a strain *Bacillus* Calmette-Guérin (BCG), which recombinantly expresses one or more proteins or immunogenic fragments of RSV.

BACKGROUND OF THE INVENTION

Among the respiratory viruses, respiratory syncytial virus (RSV) and human *Metapneumovirus* (hMPV) stand out for their clinical importance, as they can cause very severe infections in infants and young children. The clinical manifestations of both viruses are indistinguishable from each other, causing a wide range of clinical cases, which can be mild, such as rhinitis, or much more severe, such as pneumonia or bronchiolitis, with the most serious conditions being observed in infants, premature infants, children with congenital heart disease, and in immunosuppressed patients. RSV is the main causative agent of acute respiratory tract infections in infants worldwide. According to the WHO, this virus infects 64 million people annually, of which 160,000 die. RSV is the leading cause of infection and hospitalization in children under 2 years of age. (www.who.int). For its part, human *Metapneumovirus* is the second leading cause of hospitalizations due to acute respiratory infections in children under 5 years of age.

Infections caused by these viruses are extremely frequent and recurrent since practically 100% of children older than three years have presented at least one episode of RSV and/or hMPV infection at 5 years of age. Because these infections do not leave a complete immune memory, reinfections are frequent, decreasing in severity as the age of the patient increases.

The health situation generated by these respiratory infections has a high economic impact for the affected countries. Studies carried out in developed countries estimate that the individual cost of RSV infection is over 3,000 euros (approximately $2,250,000 Chilean pesos), with an upper limit of up to 8,400 euros (approximately $6,800,000 Chilean pesos).

Both RSV and hMPV are classified within the Pneumoviridae Family, a family that has two genera, *Metapneumovirus* and *Orthopneumovirus*. While hMPV belongs to the genus *Metapneumovirus*, RSV belongs to the genus *Orthopneumovirus*.

Both viruses contain non-segmented negative single-stranded RNA, with lipid envelope and similar, but not identical, organization. RSV has a genome of approximately 15 kb, with 10 genes that code for a total of 11 proteins. Five of these proteins have structural functions, corresponding to the transmembrane glycoproteins F, G, and SH, the nucleocapsid N protein, and the matrix M protein. The other four proteins, M2-1, M2-2, P, and L are involved in viral replication and transcription. The two remaining proteins, designated NS1 and NS2, are non-structural and are involved in virulence. On the other hand, hMPV has a genome of approximately 13 kb and comprises 8 genes that code for nine proteins: N, P, M1, F, M2-1, M2-2, SH, G, and L. hMPV does not contain the NS1 and NS2 proteins. The N protein is the most conserved among both viruses, RSV and hMPV.

RSV that infects humans has different strains or subtypes, with subgroups A and B being those that predominate in the population. The main antigenic difference between the subgroups corresponds to the G protein, which only conserves 40-44% of the amino acids between the different subgroups.

Due to the differences that exist between the two viruses, it is not obvious or predictable that a single vaccine could provide simultaneous protection for RSV and hMPV. As we will explain in detail later, the vaccine of the invention is a formulation containing the *Bacillus* Calmette-Guérin (BCG) strain, in a concentration of between $1 \times 10^4$ a $1 \times 10^9$ colony-forming units per dose, which expresses at least one protein or immunogenic fragment of respiratory syncytial virus (RSV). Surprisingly, the inventors have found that this immunogenic formulation confers protection against both RSV and hMPV infections.

In the state of the art, we find some unsuccessful attempts to procure a vaccine against RSV. An attempt made in the 1960s consisted of formalin-inactivated whole virus (RSV-FI), which was administered intramuscularly to volunteers in the presence of adjuvant alum (1). Contrary to expectations, this immunization produced a much more severe respiratory condition in vaccinated children after natural RSV infection, which led to the hospitalization of 80% of those vaccinated and the death of two of them (2). The respiratory-pulmonary picture presented by the vaccinated was characterized by an unusual infiltration of eosinophils and neutrophils, together with a high titer of complement-fixing antibodies (2). Analysis of the lung tissues of children vaccinated with RSV-FI who died due to RSV infection shows the deposition of complement, immune complexes, and the presence of eosinophils in the peribronchial regions (3). Along with this, studies in animal models show that vaccination with RSV-FI produces a Th2-type immune response, based on CD4+ T lymphocytes. These same characteristics have been observed in animals that have been immunized with the G protein (4) or that have received CD4+ T lymphocytes specific for this glycoprotein prior to infection with RSV.

In this same sense, the Th2 response is not capable of conferring protection against sustained viral infection over time, and stimulates, through the secretion of IL-5, the eosinophils responsible for allergic reactions and inflammatory hyper-reactivity, which can even be more dangerous than the viral infection. In this type of Th2 response, T cells also secrete IL-4, a cytokine that induces the generation of IgG1 and IgE isotype antibodies, inhibiting the IgM, IgG3, IgG2a, and IgG2b isotypes.

For these reasons, an effective and safe vaccine against RSV and hMPV respiratory viruses should generate a Th1-type immune response, based on CD4+ T helper lymphocytes and interferon-gamma (IFN-γ) secreting cytotoxic T cells. This response is capable of conferring sustained protection overtime against these viral infections, also inducing the proliferation and differentiation of B cells secreting antibodies of the IgG2a isotype and inhibiting the production of immunoglobulins of the IgG3, IgE, IgG2b, and IgG1 isotypes.

Ongoing research on RSV vaccines has focused on the analysis and development of viral subunits, such as the F proteins (5), M2 (6), and also some conserved segments of the G protein (7). On the other hand, the generation of vaccines based on mutant strains of RSV, such as those sensitive to temperature (8), with deletion of some genes (9) or recombinants for cytokines such as GM-CSF (10) have also been studied. Some of these vaccines have been tested in phase I and II clinical trials, with variable results (11-13). Another type of tentative vaccine against RSV is the case of vaccines based on proteins F and G, which are administered with adjuvants such as ISCOMs. Immunization with this type of vaccine produces an increased infiltration of eosinophils in the lung tissue against a new viral infection (14), which increases the damage in the lung tissue.

The infant's immune system is characterized by preferentially developing Th2-type immune responses, possibly due to the immaturity of the immune system during the first six months of life (15, 16). However, if properly stimulated, it can mount a Th1-type response (17).

In order to formulate an effective and safe vaccine against RSV and/or hMPV, the inventors have carried out a finished study of the immune response generated against the different RSV proteins, in order to identify those that allow the generation of a Th1-type immune response, based on cytotoxic T lymphocytes. The use of bacterial vectors for the heterologous expression of viral antigens has the advantage that they can be used as live attenuated vectors since they have their invasion capacities intact and are recognized as non-pathogenic. An additional advantage of certain bacterial vectors used for the expression of heterologous antigens is their recognized ability to induce Th1-type immunities (18, 19), which is highly attractive in the case of vaccine development. *Bacillus* Calmette-Guérin (BCG) is an attenuated strain of *Mycobacterium bovis* that is used as a vaccine in newborns against *Mycobacterium tuberculosis*. Since BCG was approved as a tuberculosis vaccine, it has been given to more than 3.3 billion people around the world. Its massive use has been facilitated by several advantageous characteristics of this bacterium, such as its great thermostability in the lyophilized form. Furthermore, immunizing newborn infants with this bacterium is not risky and produces only minimal side effects. Regarding the safety and stability of BCG reversion to virulence has never been observed over all the years it has been in use. BCG is highly immunogenic and with just one dose it is possible to generate an immune response that is maintained for long periods. Importantly, BCG induces a potent Th1-type immune response in both adults and children (20). This phenomenon in neonates is evidenced by the cellular-type immune response that is generated against *M. tuberculosis* antigens (PPD), a response that manages to be maintained for prolonged periods (20).

To date, several bacterial, parasitic, and viral antigens have been successfully expressed in this bacterial system, which when evaluated in animal models have been shown to be capable of generating humoral and cellular immunity against these antigens (21, 22). In addition, BCG has the particularity of not being neutralized by antibodies present in breast milk, so it can be used as an immunity inducer in nursing children (22). The present invention corresponds to an immunological formulation that contains one or more attenuated recombinant strains of *Mycobacterium*, bacteria, preferably the BCG strain, for RSV proteins and can be used in the preparation of vaccines against respiratory viruses, especially RSV and hMPV.

The formulation of the invention makes it possible to avoid or attenuate the lung damage caused by infection by the respiratory viruses RSV and hMPV, thanks to the generation of an efficient and favorable immune response for the elimination of the virus. Because attenuated strains of *Mycobacterium*, such as BCG, are potent inducers of Th1-type immune responses, the immune response induced by recombinant BCG strains for RSV provides protection against infections caused both viruses.

BRIEF DESCRIPTION OF THE INVENTION

The present invention consists of an immunogenic formulation that induces protection against infection caused by respiratory viruses, especially infections caused by respiratory syncytial virus (RSV) and/or human *Metapneumovirus* (hMPV), or at least attenuates the pathologies caused by these viruses in mammals. The immunogenic formulation of the present invention can be used to prepare vaccines and contains colony forming units (CFU) of live attenuated recombinant strains of *Mycobacterium*, preferably the *Bacillus* Calmette-Guérin (BCG) strain that recombinantly or heterologously express one or more proteins or immunogenic fragments of respiratory syncytial virus.

These proteins or immunogenic fragments of RSV correspond to the RSV NS1, NS2, N, P, M, SH, M2 (ORF1), M2 (ORF2), L, F or G proteins of the RSV A or RSV B subtypes and are found inserted either in the bacterial genome of the attenuated strains of *Mycobacterium* or in extrachromosomal plasmids, in one or more copies, and their expression is managed by endogenous or exogenous, constitutive or inducible, BCG promoters. These proteins or immunogenic fragments of RSV can be expressed by BCG or other attenuated strains of *Mycobacterium*, in soluble-cytoplasmic form, secreted extracellularly or as proteins bound to the cell membrane.

The immunogenic formulation disclosed in the present invention can be used in conjunction with immunogenic formulations that contain other attenuated strains of *Mycobacterium* or BCG and that differ in the immunogenic RSV proteins that they express, as well as in the location of the genes (inserted in the genome or extrachromosomal), the number of copies of the gene protein, the promoter that induces the expression of the protein, or the destination of the RSV immunogenic protein or fragments (soluble-cytoplasmic, extracellularly secreted or cell membrane-bound proteins).

The immunogenic formulation described above is useful for preparing a vaccine, which can be applied to the individual subcutaneously, percutaneously, or subdermally, in conjunction with a buffered or physiological saline solution.

The immunogenic formulation of the invention can be used to vaccinate individuals who have or have not had previous contact with a respiratory syncytial virus or human *Metapneumovirus*, to confer protection against respiratory viruses, such as RSV and/or hMPV.

DESCRIPTION OF THE FIGURES

FIG. 1 shows the percentage of CD8+/CD69+ cells (A) and (B) IFN-$\gamma$ secretion of cells from the spleen of BALB/c mice immunized with BCG in saline solution ((PBS: 137 mM NaCl; 2.7 mM KCl; 4.3 mM Na$_2$HPO$_4$; 1.47 mM KH$_2$PO$_4$, TWEEN 80® (polysorbate 80; a non-ionic surfactant) 0.02% pH 7.4, a 4° C.) that expresses the N protein. 5×10$^5$ cells from the spleen of unimmunized animals, immunized with 1×10$^7$ PFU of RSV, immunized with BCG (1×10$^8$ CFU/mouse in PBS: 137 mM NaCl; 2.7 mM KCl; 4.3 mM Na$_2$HPO$_4$; 1.47 mM KH$_2$PO$_4$, TWEEN 80® 0.02% pH 7.4, 4° C.) or immunized with recombinant BCG for the RSV N protein (1×10$^8$ CFU/mouse in PBS: 137 mM NaCl; 2.7 mM KCl; 4.3 mM Na$_2$HPO$_4$; 1.47 mM KH$_2$PO$_4$, TWEEN 80® 0.02% pH 7.4, 4° C.) stimulated for 72 hrs. with 0.5 μM of RSV N protein. Subsequently, the percentage of positive cells for the CD8 and CD69 (A) markers was determined by flow cytometry. Cell supernatants were subjected to ELISA to detect the presence of secreted IFN-γ. (B) **, p value 0.002, Student's t-test. It can be concluded that the recombinant BCG strain for the RSV N protein produces, in mice immunized with this immunogenic formulation, a favorable response by T lymphocytes.

These results show that in response to immunization with recombinant BCG for RSV N protein, these CD8+ T lymphocytes are activated, since they express activation markers on their surface (CD69+) and secrete IFN-γ to the extracellular medium, which evidence that the vaccine of the invention generates a Th1-type immune response.

Figure 2:
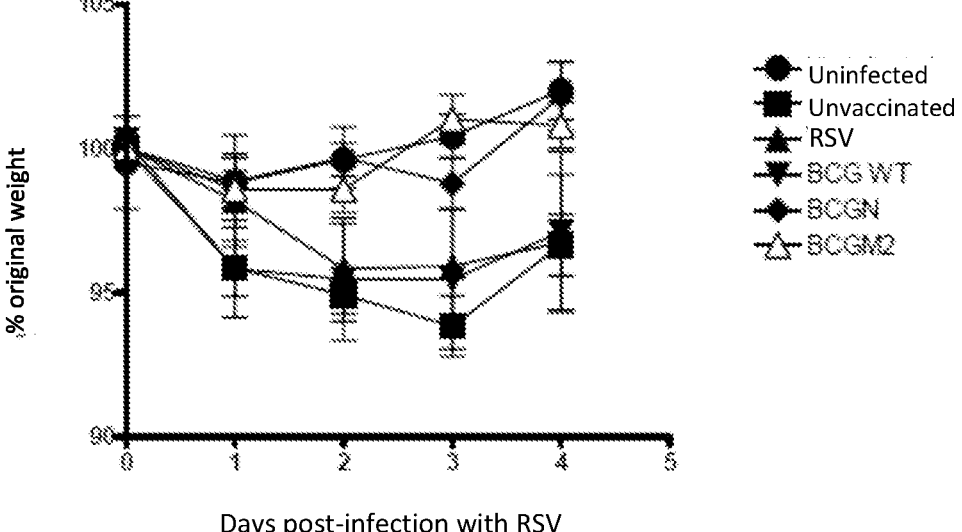

FIG. 2 shows a curve of body weight variation of BALB/c mice immunized with a recombinant BCG strain that express RSV N protein ($1 \times 10^8$ CFU/mouse, in PBS: 137 mM NaCl; 2.7 mM KCl; 4.3 mM $Na_2HPO_4$; 1.47 mM $KH_2PO_4$, TWEEN 80® 0.02% pH 7.4, 4° C.) or with a recombinant BCG strain for RSV M2 protein ($1 \times 10^8$ CFU/mouse, in PBS: 137 mM NaCl; 2.7 mM KCl; 4.3 mM $Na_2HPO_4$; 1.47 mM $KH_2PO_4$, TWEEN 80® 0.02% pH 7.4, 4° C.). Unvaccinated BALB/c mice (■) immunized with $1 \times 10^7$ plaque-forming units (PFU) of UV-inactivated RSV (UV Bulb, 312 nm, power 8 watts) for 20 minutes (RSV-UV) (▲), immunized with a strain of wild BCG (WT), which does not express RSV (▼) ($1 \times 10^8$ CFU/mouse, in PBS: 137 mM NaCl; 2.7 mM KCl; 4.3 mM $Na_2HPO_4$; 1.47 mM $KH_2PO_4$, TWEEN 80® 0.02% pH 7.4, 4° C.), immunized with a BCG strain transformed with pMV361-N (□) ($1 \times 10^8$ CFU/mouse, in PBS: 137 mM NaCl; 2.7 mM KCl; 4.3 mM $Na_2HPO_4$; 1.47 mM $KH_2PO_4$, TWEEN 80® 0.02% pH 7.4, 4° C.) or immunized with a BCG strain transformed with pMV361-M2 (Δ) ($1 \times 10^8$ CFU/mouse, in PBS: 137 mM NaCl; 2.7 mM KCl; 4.3 mM $Na_2HPO_4$; 1.47 mM $KH_2PO_4$, TWEEN 80® 0.02% pH 7.4, 4° C.) were infected intranasally with $1 \times 10^7$ PFU of RSV, strain 13018-8. As a control, a group of unvaccinated and uninfected mice (●) was included. The variation in body weight with respect to day 0 was recorded daily for 4 days. **, p-value 0.002, Student's t-test.

It can be concluded that the immunization of mice with a recombinant BCG strain for RSV N or M2 proteins produces a favorable response against RSV infection since postinfection the body weight of these mice does not vary significantly when compared to that of unvaccinated mice, in which a decrease in body weight is observed postinfection.

FIG. 3-A shows the percentage of $CD11c^+/CD11b^+/Gr1^+$ cells in bronchoalveolar lavage of BALB/c mice from four experimental groups: unimmunized and uninfected, unimmunized and intranasally infected with $1 \times 10^7$ of hMPV strain cz0107, mice immunized with BCG recombinant for the RSV N protein ($1 \times 10^8$ CFU/mouse) and mice immunized with recombinant BCG for hMPV P protein ($1 \times 10^8$ CFU/mouse).

It is observed that the groups immunized with the recombinant BCG strain for the P protein of hMPV and the N protein of RSV show significantly less polymorphonuclear infiltration than the infected group without immunization.

FIG. 3-B shows the percentage of $CD11c^-/CD11b^+/Gr1^+$ cells in the lung for the four groups studied.

As in the previous case, it is observed that the groups immunized with the recombinant BCG strain for the P protein of hMPV and the N protein of RSV show significantly less infiltration of inflammatory cells than that of the infected group without immunization. It can be seen that the group immunized with the recombinant BCG for hMPV P even shows a similar result to that of the uninfected control group (1).

Figure 4:
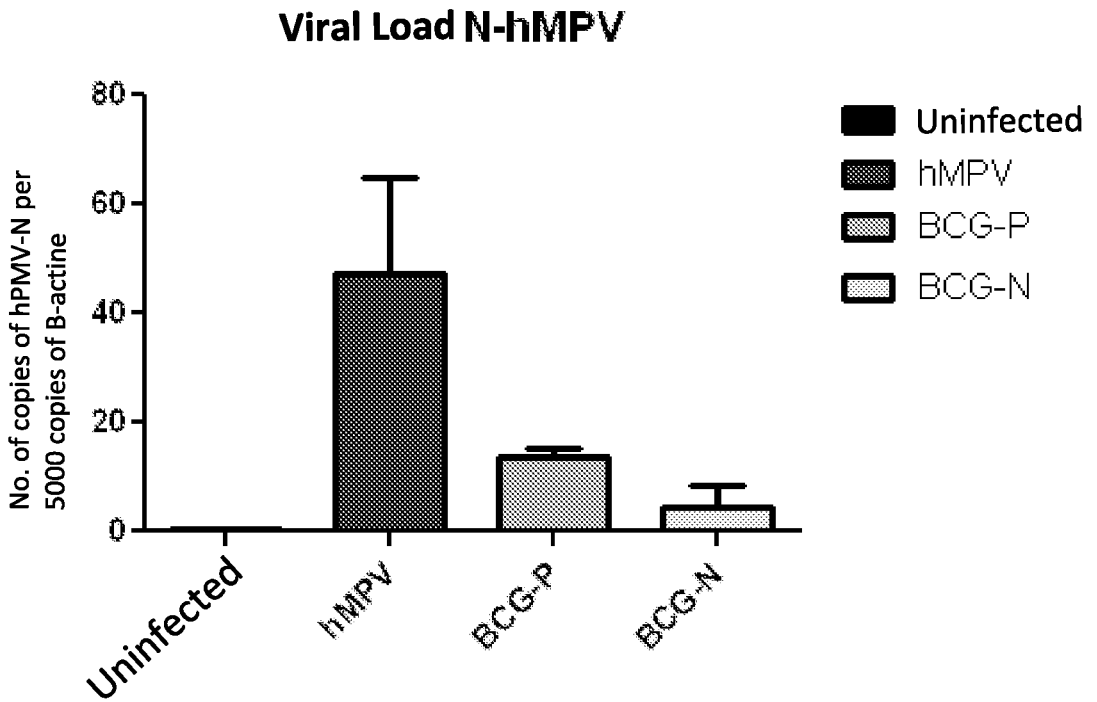

FIG. 4 shows the viral load in lung tissue evaluated by qPCR for the four study groups, expressed as the number of copies of the hMPV N protein per 5,000 copies of β-actin. It is observed that the groups immunized both with the recombinant BCG strain for hMPV P protein and with the recombinant BCG for RSV N have a significantly lower viral load than the unimmunized infected group.

Figure 5:
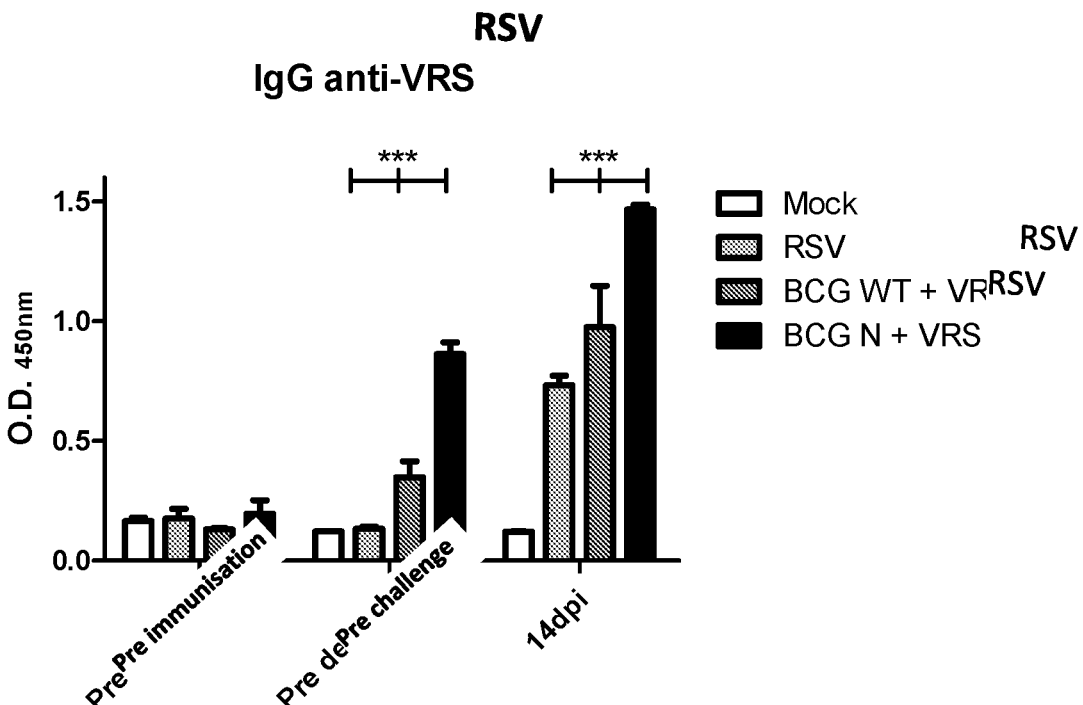

FIG. 5 shows the levels of specific antibodies against RSV (expressed in O.D. 450 nm) evaluated by ELISA in sera of animals immunized with the recombinant BCG-N vaccine, at three different time points: day 0 (pre-immune), day 21 (pre-viral challenge), and day 14 post-infection.

The results show that animals immunized with BCG-N produce anti-RSV antibodies even before the viral challenge. After the challenge with RSV, the levels of specific IgG immunoglobulins against the virus are significantly higher in the group of animals immunized with BCG-N in relation to the control groups.

Figure 6:
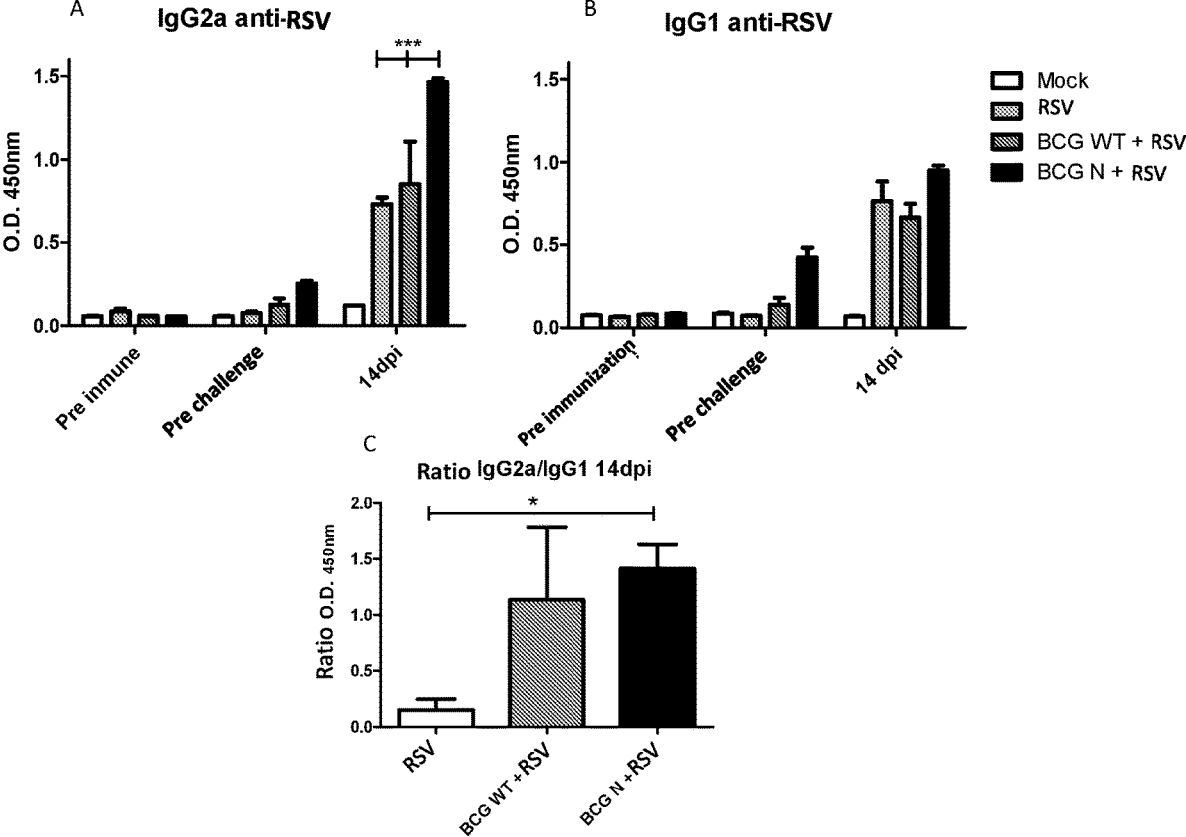

FIG. 6 shows the isotype characterization of the specific antibodies against RSV induced by the recombinant BCG-N vaccine, expressed in O.D. 450 nm, in sera from immunized and non-immunized animals evaluated by ELISA. The isotype of the immunoglobulins was analyzed by specific secondary antibodies against IgG2a (FIG. 6A) or IgG1 (FIG. 6B) at three different times. FIG. 6C shows the ratio of O.D. 450 nm of IgG2a on IgG1 from data obtained by ELISA at day 14 post-infection. It is shown that the ratio of anti-RSV immunoglobulins of isotype IgG2a/IgG1 after the infection is higher in animals immunized with the vaccine of the invention BCG N.

Figure 7:
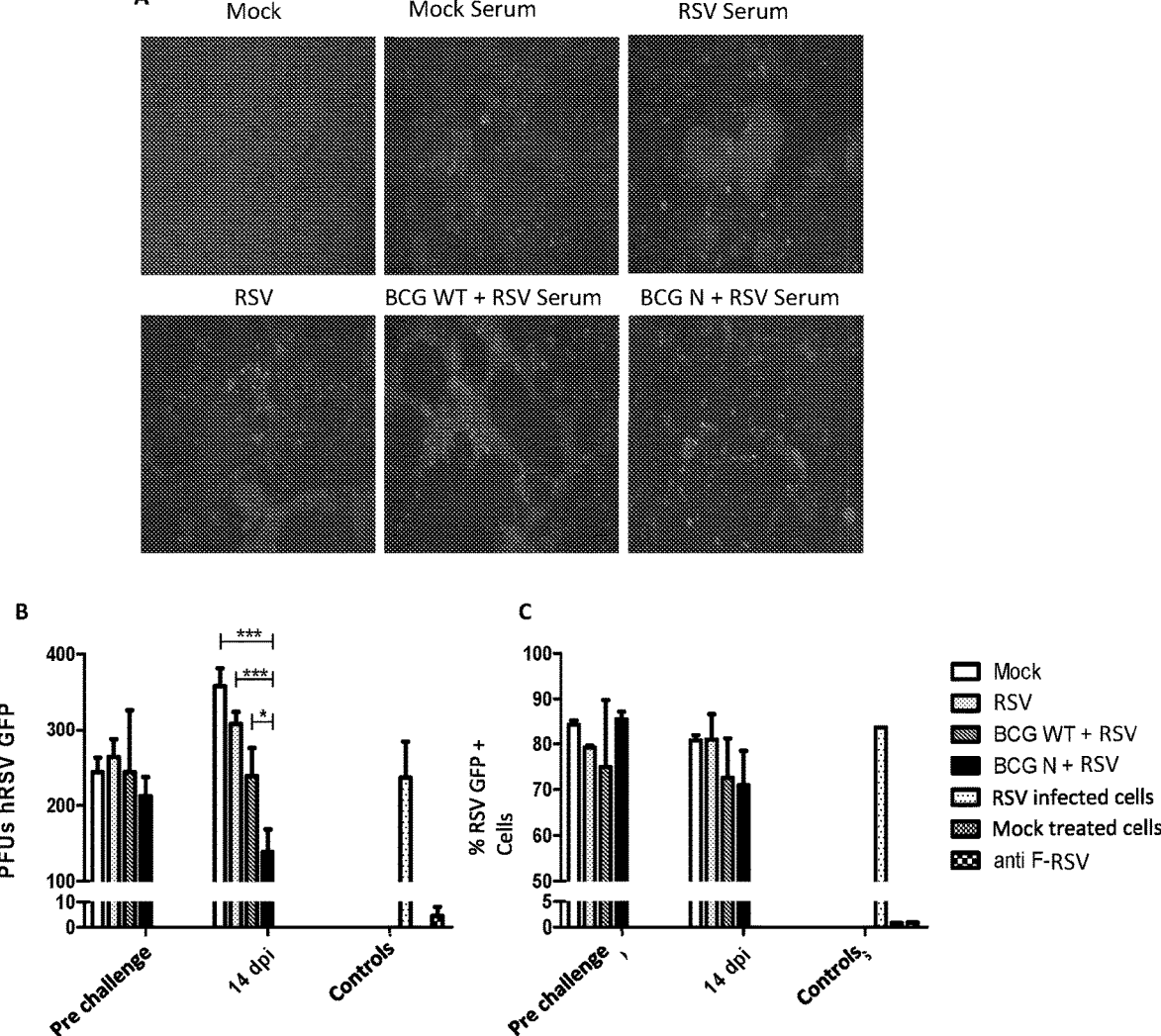

FIG. 7 shows an RSV-GFP seroneutralization assay in HEp-2 cells. FIG. 7A HEp-2 cells were treated with a mixture of serum and RSV-GFP previously incubated at 37° C. for 1 hour and after 48 hours they were visualized in an epifluorescence microscope. FIG. 7 B Quantification of plaque-forming units (PFUs) visualized by microscopy. FIG. 7 C Quantification of GFP expression in HEp-2 cells by flow cytometry. The absence of bars in B and C indicates that viral GFP was not detected in the treated cells.

It is evident that the antibodies produced by immunization with the vaccine of the invention are capable of reducing RSV infection in vitro, for which reason these immunoglobulins possess neutralizing functions against the respiratory syncytial virus.

Figure 8:
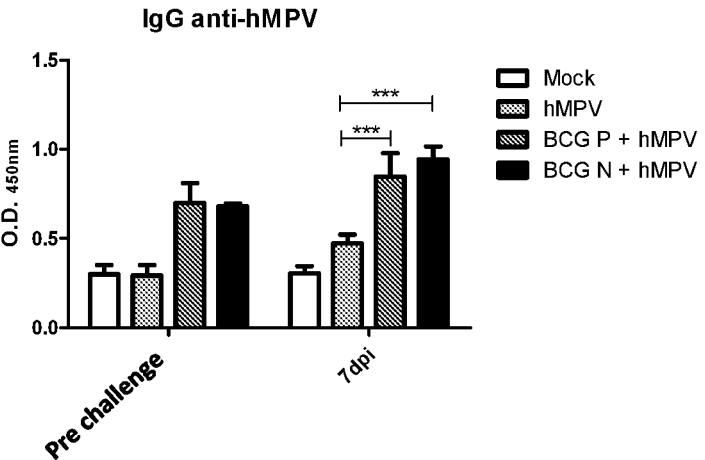

FIG. 8 shows the levels of specific antibodies against hMPV (expressed in O.D. 450 nm), in sera of animals immunized with the recombinant vaccine BCG-N, BCG-P, and unimmunized and uninfected controls (Mock), at two different times: day −21 (pre viral challenge) and day 7 post-infection.

The results show that immunization with recombinant BCG for the RSV N protein induces an increase in the levels of specific IgG against hMPV before and after viral challenge, in the same proportion as immunization with recombinant BCG for P of hMPV.

DETAILED DESCRIPTION OF THE INVENTION

The present invention consists of an immunogenic formulation that can be used for the preparation of vaccines that induce protection against infections caused by respiratory viruses, specifically, respiratory syncytial virus and/or human *Metapneumovirus*, or that attenuate the pathologies caused by these viruses in mammals. The vaccines of the invention contain live attenuated recombinant strains of *Mycobacterium*, preferably *Bacillus* Calmette-Guérin (BCG), for example, the BCG Danish or Pasteur strains that recombinantly or heterologously express one or more proteins or immunogenic fragments of RSV. The vaccines of the invention comprise between $1\times10^4$-$1\times10^9$ CFU (colony forming units) of the strains described per dose and can be preserved, before administration, in a lyophilized form or a cold stabilizing saline solution.

Examples of appropriate stabilizer solutions for the immunogenic formulations or vaccines of the invention are:

Sauton SSI diluted solution (125 µg MgSO$_4$, 125 µg K$_2$HPO$_4$, 1 mg L-asparagine, 12.5 µg ferric ammonium citrate, 18.4 mg 85% glycerol, 0.5 mg citric acid, in 1 ml of H$_2$O) at 4° C., PBS (137 mM NaCl; 2.7 mM KCl; 4.3 mM Na$_2$HPO$_4$; 1.47 mM KH$_2$PO$_4$, pH 7.4) supplemented with TWEEN 80® 0.02% and Glycerol 20% at −80° C. or Volume solution: volume of lactose 25% and Proskauer and Beck's Medium supplemented with glucose and TWEEN 808 (PBGT: 0.5 g asparagine; 5.0 g monopotassium phosphate; 1.5 g magnesium citrate; 0.5 g potassium sulphate; 0.5 ml TWEEN 80® and 10.0 g glucose per liter of distilled water) lyophilized and stored at a temperature range of between 4° C. and 25° C.

The attenuated recombinant *Mycobacterium* bacteria of the immunogenic formulation of the present invention contain genes encoding for at least one RSV protein, or immunogenic fragment of the RSV A or RSV B subtypes or both. The respiratory syncytial virus genome has been previously described in the GeneBank database, access numbers NC-001803 and NC-001781.

Where the genes encoding at least one RSV protein, or immunogenic fragment of the RSV A or RSV B subtypes or both of the present invention have at least 80% identity with the genes described in said GeneBank disclosed sequences, access numbers NC-001803 and NC-001781.

The RSV immunogenic proteins, or fragments, corresponding to the RSV NS1, NS2, N, P, M, SH, M2 (ORF1), M2 (ORF2), L, F, or G proteins. In a preferred embodiment, the immunogenic proteins or fragments correspond to N, P, M, SH, M2 (ORF1), M2 (ORF2), L, F or G of RSV.

To obtain the recombinant strains of the invention, the genes that code for these proteins or their immunogenic fragments are inserted into a plasmid, which is incorporated into the bacterium by any available technique. In one embodiment, the plasmid pMV361 is used, it is incorporated into the bacterium by electro transformation, and it is integrated into the bacterial genome by the action of mycobacteriophage integrases (23). These genes can also be inserted into extrachromosomal plasmids, such as pMV261, which is incorporated into *Mycobacterium* by electrotransformation and remains extrachromosomal in bacteria (23). These genes can be in one or more copies, and their expression is controlled by endogenous, constitutive or inducible, promoters of BCG, for example, the promoter of the hsp60 gene and the promoter of the acr gene respectively. These proteins, or immunogenic fragments of RSV, can be expressed by BCG or other attenuated strains of *Mycobacterium*, in a soluble-cytoplasmic way, secreted extracellularly or as proteins bound to the cell membrane thanks to the fusion of the genes of the respiratory syncytial virus, or immunogenic fragments, with DNA sequences that code for peptides that function as targeting signals of proteins to the different bacterial compartments, for example, the N-terminal sequence of the gene for the alpha-antigen for extracellular secretion and the N-terminal sequence of the gene for the 19 kD protein for membrane-bound proteins.

The immunogenic formulation disclosed in the present invention can be used in conjunction with immunogenic formulations that contain one or more attenuated strains of *Mycobacterium* or BCG and that differ in the immunogenic RSV proteins that they express, as well as in the location of the genes (inserted into the genome or extrachromosomal), the number of copies of the protein gene, the promoter that induces the expression of the protein, or the target of the RSV immunogenic protein or fragments (soluble-cytoplasmic, extracellularly secreted or proteins bound to the cellular membrane).

The inventors have shown that the vaccines of the invention induce a Th1-type immune response, which includes both IgG2a isotype antibody-producing B lymphocytes, and an efficient IFN-γ-producing T lymphocyte response. This guarantees humoral protection against these respiratory viruses and an efficient cellular response that enhances both the effectiveness and the applicability of the immunogenic formulation of the invention.

The vaccine of the invention can be administered to the individual subcutaneously, percutaneously, or subdermally, in conjunction with a buffered or physiological saline solution.

As indicated, the immunogenic formulation of the invention can be used to vaccinate individuals who have or have not had previous contact with a respiratory virus such as respiratory syncytial virus or human *Metapneumovirus*, in order to confer protection against these respiratory viruses or to attenuate the pathology caused by these in the future.

The following examples are applicable to immunological formulations containing an attenuated recombinant strain of *Mycobacterium* expressing the NS2, N, P, M, SH, M2 (ORF1), M2 (ORF2), L, F or G proteins of RSV, and also all combinations of these formulations. Likewise, the examples are applicable to immunological formulations containing one or more attenuated recombinant strains of *Mycobacterium*; where said recombinant bacteria contain protein genes, or immunogenic fragments of RSV that are inserted in the bacterial genome or in extrachromosomal plasmids, in one or more copies, and their expression is managed by endogenous or exogenous, constitutive or inducible, expressed promoters, in a soluble-cytoplasmic form, secreted extracellularly or as proteins bound to the cell membrane.

EXAMPLES

These examples are illustrative only and are not intended to limit the range of production or application of the invention. Although specific terms are used in the following descriptions, their use is descriptive only and not limiting.

Example 1: Immunogenic Formulation Consisting of $10^8$ Bacteria of the Recombinant Danish BCG Strain for the N Gene of RSV Subtype A The gene is inserted in a copy in the genome of the bacterium under the regulation of the constitutive endogenous promoter hsp60 of BCG and the expression of the protein is cytoplasmic. The immunogenic formulation can be found in a diluted Sauton SSI solution (125 µg MgSO$_4$, 125 µg K$_2$HPO$_4$, 1 mg L-asparagine, 12.5 µg ferric ammonium citrate, 18.4 mg 85% glycerol, 0.5 mg citric acid in 1 ml of $H_2O$) at –80° C. The formulation can also be found in a PBS solution (137 mM NaCl; 2.7 mM KCl; 4.3 mM $Na_2HPO_4$; 1.47 mM $KH_2PO_4$, pH 7.4), supplemented with 20% Glycerol and TWEEN 80® 0.02% at a final concentration of $10^8$ bacteria per 100 µl and stored at –80° C. In the same way, the strains can be resuspended in a volume solution: volume of lactose 25% and Proskauer and Beck Medium supplemented with glucose and TWEEN 80® (PBGT: 0.5 g asparagine; 5.0 g monopotassium phosphate; 1.5 g citrate magnesium; 0.5 g potassium sulfate; 0.5 ml TWEEN 80® and 10.0 g glucose per liter of distilled water) to later be lyophilized and stored at 25° C.

The Danish BCG strain was transformed by electrotransformation (24) with the plasmid pMV361/N, derived from the plasmid pMV361 (25), which is inserted only once into the genome of the bacterium. This plasmid contains the gene coding for the RSV N protein subtype A, which is expressed under the endogenous and constitutive promoter of the BCG hsp60 gene. The resulting recombinant colonies were grown (at 37° C. in supplemented Middlebrock 7H9 culture medium) until $OD_{600\ nm}$=1, they were centrifuged at 4,000 rpm for 20 min (eppendorf rotor model 5702/R A-4-38) and resuspended in solution. PBS (137 mM NaCl; 2.7 mM KCl; 4.3 mM $Na_2HPO_4$; 1.47 mM $KH_2PO_4$, pH 7.4), supplemented with 20% Glycerol and 0.02% TWEEN 80® at a final concentration of $10^8$ bacteria per 100 µl and stored at –80° C. In the same way, the strains can be resuspended in a volume solution: volume of lactose 25% and Proskauer and Beck Medium supplemented with glucose and TWEEN 803 (PBGT: 0.5 g asparagine; 5.0 g monopotassium phosphate; 1.5 g citrate magnesium; 0.5 g potassium sulfate; 0.5 ml TWEEN 80® and 10.0 g glucose per liter of distilled water) to later be lyophilized and stored at 25° C. By Western blot, using antibodies to RSV N protein, the inventors observed that this BCG strain recombinantly expresses the RSV N protein subtype A in the cytoplasm. Immunization of BALB/c mice with the described formulation, as a vaccine, confers protection of these animals against an intranasal infection with $10^7$ plaque-forming units of RSV subtype A (FIGS. 1 y 2). This immunogenic formulation can confer immunity against RSV N protein subtype A and B.

Example II: Immunogenic Formulation Consisting of $5 \times 10^7$ Bacteria of the Recombinant Danish BCG Strain for the N Gene of RSV Subtype A and $5 \times 10^7$ Bacteria of the Recombinant Danish BCG Strain for the M2 Gene of RSV Subtype A In each of the bacteria that make up the immunogenic formulation, the RSV genes are inserted in a copy in the genome of the bacterium under the regulation of the constitutive endogenous promoter hsp60 of BCG and the expression of the protein is cytoplasmic. The immunogenic formulation is preserved in PBS (137 mM NaCl; 2.7 mM KCl; 4.3 mM $Na_2HPO_4$; 1.47 mM $KH_2PO_4$, pH 7.4), supplemented with Glycerol 20% and TWEEN 80® 0.02% a final concentration of $10^8$ bacteria per 100 µl and they were stored at –20° C. In the same way, the strains can be resuspended in a volume solution: lactose 25% and Proskauer and Beck Medium supplemented with glucose and TWEEN 80® (PBGT: 0.5 g asparagine; 5.0 g monopotassium phosphate; 1.5 g citrate magnesium; 0.5 g potassium sulfate; 0.5 ml TWEEN 80 and 10.0 g glucose per liter of distilled water) to later be lyophilized and stored at 4° C.

The Danish BCG strain was transformed, by electrotransformation (24) with the plasmid pMV361/N or pMV361/M2, derived from the plasmid pMV361 (25), which are inserted only once into the genome of the bacterium. These plasmids contain the genes for the RSV subtype A proteins N and M2 respectively, under the constitutive promoter of the BCG hsp60 gene. The resulting recombinant colonies were grown at 37° C. in supplemented Middlebrock 7H9 culture medium until $OD_{600\ nm}$=1, were centrifuged at 4000 rpm for 20 min (eppendorf rotor model 5702/R A-4-38) and were resuspended in a solution PBS (137 mM NaCl; 2.7 mM KCl; 4.3 mM $NazHPO_4$; 1.47 mM $KH_2PO_4$, pH 7.4), supplemented with 20% Glycerol and 0.02% TWEEN 80® at a final concentration of $10^7$ bacteria per 100 µl and stored at –20° C. In the same way, the strains can be resuspended in a volume solution: lactose 25% and Proskauer and Beck Medium supplemented with glucose and TWEEN 80® (PBGT: 0.5 g asparagine; 5.0 g monopotassium phosphate; 1.5 g citrate magnesium; 0.5 g potassium sulfate; 0.5 ml TWEEN 80® and 10.0 g glucose per liter of distilled water) to later be lyophilized and stored at 4° C. By Western blot, with the use of antibodies to RSV proteins N and M2, the inventors observed that these BCG Danish strains recombinantly express RSV subtype A proteins N and M2. This immunogenic formulation can confer simultaneous immunity against the M2 and N proteins of RSV subtype A and B.

Example III: Immunogenic Formulation Consisting of 106 Bacteria of the Recombinant Pasteur BCG Strain for a Segment of the F Protein of RSV Subtype B The gene is found in bacteria extrachromosomally in multiple copies (2-4 copies per bacterium) and codes for a fragment of the RSV subtype B protein F (segment ranging from amino acid 5 to 200). The expression of this gene is under the control of the constitutive endogenous promoter of the gene encoding the alpha-antigen protein (85 kD) of BCG. Furthermore, the protein encoded by this gene has, at its N-terminal end, the peptide signal (SEQ ID NO: 32)
HMKKRGLTVAVAGAAILVAGLSGCSSNKSTTGSGETTTTAAGTTASPGG of the 19 kDa protein of BCG, which induces its expression in the bacterial membrane. The immunogenic formulation is preserved in PBS (137 mM NaCl; 2.7 mM KCl; 4.3 mM $Na_2HPO_4$; 1.47 mM $KH_2PO_4$, pH 7.4) supplemented with TWEEN 80® 0.02% and Glycerol 20% at –80° C. In the same way, the strains can be resuspended in a volume solution: lactose 25% and Proskauer and Beck Medium supplemented with glucose and TWEEN 80® (PBGT: 0.5 g asparagine; 5.0 g monopotassium phosphate; 1.5 g citrate magnesium; 0.5 g potassium sulfate; 0.5 ml TWEEN 80® and 10.0 g glucose per liter of distilled water) to later be lyophilized and stored at 4° C.

The Pasteur BCG strain was transformed, by electrotransformation (24) with the plasmid pMV261/$F_{5-200}$, derived from the plasmid pMV261 (25), which resides extrachromosomally in multiple copies in the bacterium. This plasmid encodes a fragment of the F gene of RSV subtype B (a segment that goes from amino acid 5 to 200) fused at its N-terminal end with the peptide signal:

(SEQ ID NO: 32)
HMKKRGLTVAVAGAAILVAGLSGCSSNKSTTGSGETTTTAAGTTASPGG of the 19 kD protein of BCG, which induces its expression in the bacterial membrane. The expression of this gene is under the control of the constitutive endogenous promoter of the gene encoding the alpha antigen protein (85 kD) of BCG. The resulting recombinant colonies were grown up to $OD_{600\ nm}=1$, at 37° C. in supplemented Middlebrock 7H9 culture medium and were centrifuged at 4,000 rpm for 20 min (eppendorf rotor model 5702/R A-4-38) and resuspended in PBS (137 mM NaCl; 2.7 mM KCl; 4.3 mM $Na_2HPO_4$; 1.47 mM $KH_2PO_4$, pH 7.4) supplemented with TWEEN 80® 0.02% and Glycerol 20% at a final concentration of 106 bacteria per 100 µl. In the same way, the strains can be resuspended in a volume solution: volume of lactose 25% and Proskauer and Beck Medium supplemented with glucose and TWEEN 80® (PBGT: 0.5 g asparagine; 5.0 g monopotassium phosphate; 1.5 g citrate magnesium; 0.5 g potassium sulfate; 0.5 ml TWEEN 80® and 10.0 g glucose per liter of distilled water) to later be lyophilized in aliquots with 106 bacteria each and stored at 4° C. This immunogenic formulation can confer immunity against the F protein of RSV subtype A and B.

Example IV: Immunogenic Formulation Consisting of $10^5$ Bacteria of the Recombinant Danish BCG Strain Simultaneously for the N and M2 Genes of RSV Subtype A The N gene is inserted in a copy in the genome of the bacterium under the regulation of the constitutive endogenous promoter hsp60 of BCG and the expression of the protein is cytoplasmic. The M2 gene is found extrachromosomally in the bacterium in multiple copies (2-4 copies per bacterium) under the control of the constitutive endogenous promoter of the gene encoding the alpha antigen protein (85 kD) of BCG. The protein encoded by the M2 gene has, at its N-terminal end, the peptide signal (SEQ ID NO: 32)
HMKKRGLTVAVAGAAILVAGLSGCSSNKSTTGSGETTTTAAGTTASPGG of the 19 kDa protein of BCG, which induces its expression in the bacterial membrane. The immunogenic formulation is preserved at 4° C. lyophilized from the bacteria resuspended in a solution volume: lactose 25% and Proskauer and Beck Medium supplemented with glucose and TWEEN 80® (PBGT: 0.5 g asparagine; 5.0 g monopotassium phosphate; 1.5 g magnesium citrate; 0.5 g potassium sulfate; 0.5 ml TWEEN 80® and 10.0 g glucose per liter of lyophilized distilled water stored at 4° C. Similarly, the strains can be preserved in a PBS solution (137 mM NaCl; 2.7 mM KCl; 4.3 mM $Na_2HPO_4$; 1.47 mM $KH_2PO_4$, pH 7.4) supplemented with TWEEN 80® 0.02% and Glycerol 20% at a final concentration of $10^5$ bacteria per 100 µl.

The Danish BCG strain was transformed by electrotransformation (24) with the plasmid pMV361/N, derived from the plasmid pMV361 (25), which is inserted only once into the genome of the bacterium. This plasmid contains the gene coding for the RSV N protein subtype A, which is expressed under the endogenous and constitutive promoter of the BCG hsp60 gene. After verifying that the resulting BCG strain is recombinant for the RSV N protein, it was transformed by electrotransformation (24) with the plasmid pMV206/M2, derived from the plasmid pMV206 (25), which resides extrachromosomally in multiple copies in the bacteria. The protein encoded by the M2 gene has, at its N-terminal end, the peptide signal (SEQ ID NO: 32)
HMKKRGLTVAVAGAAILVAGLSGCSSNKSTTGSGETTTTAAGTTASPGG of the 19 kD protein of BCG, which induces its expression in the bacterial membrane. The resulting recombinant colonies were grown (at 37° C. in supplemented Middlebrock 7H9 culture medium) until $OD_{600\ nm}=1$, were centrifuged at 4,000 rpm for 20 min (eppendorf rotor model 5702/R A-4-38) and were resuspended in a solution volume: lactose 25% and Proskauer and Beck's Medium supplemented with glucose and TWEEN 80® (PBGT: 0.5 g asparagine; 5.0 g monopotassium phosphate; 1.5 g magnesium citrate; 0.5 g sulfate of potassium; 0.5 ml TWEEN 80® and 10.0 g glucose per liter of distilled water) at a final concentration of $10^5$ bacteria per 1 ml. Finally, 1 ml aliquots were lyophilized with $10^5$ bacteria and the aliquots were stored at 4° C. Similarly, the strains can be preserved in a PBS solution (137 mM NaCl; 2.7 mM KCl; 4.3 mM $Na_2HPO_4$; 1.47 mM $KH_2PO_4$, pH 7.4) supplemented with TWEEN 80® 0.02% and Glycerol 20% at a final concentration of $10^5$ bacteria per 100 µl. This immunogenic formulation can confer immunity against the N and M2 proteins of RSV subtype A and B.

Example V: Immunogenic Formulation Consisting of $10^4$ Bacteria of the Recombinant Danish BCG Strain for the N Gene of RSV Subtype A The gene is inserted in one copy in the bacterial genome under the regulation of the endogenous inducible acr promoter of BCG, which is active in response to nitric oxide, low oxygen concentrations, and stationary phases of growth. The expression of the protein is cytoplasmic. The immunogenic formulation is lyophilized from a volume: volume solution of 25% lactose and Proskauer and Beck Medium supplemented with glucose and TWEEN 80® (PBGT: 0.5 g asparagine; 5.0 g monopotassium phosphate; 1.5 g citrate. magnesium; 0.5 g potassium sulfate; 0.5 ml TWEEN 80® and 10.0 g glucose per liter of distilled water) stored at 25° C. in dilute Sauton SSI solution (125 µg $MgSO_4$, 125 µg $K_2HPO_4$, 1 mg L-asparagine, 12.5 µg ferric ammonium citrate, 18.4 mg 85% glycerol, 0.5 mg citric acid in 1 ml of $H_2O$). Similarly, the strains can be preserved in a PBS solution (137 mM NaCl; 2.7 mM KCl; 4.3 mM $Na_2HPO_4$; 1.47 mM $KH_2PO_4$, pH 7.4) supplemented with TWEEN 80® 0.02% and Glycerol 20% at a final concentration of $10^4$ bacteria per 100 µl.

The Danish BCG strain was transformed by electrotransformation (24) with the plasmid pMV361$_{Pacr}$/N, derived from the plasmid pMV361 (25), which is inserted only once into the genome of the bacterium. This plasmid contains the gene that codes for the RSV N protein subtype A, which is expressed under the endogenous and inducible promoter of the BCG acr gene (26). The resulting recombinant colonies were grown (at 37° C. in supplemented Middlebrock 7H9 culture medium) until $OD_{600\ nm}=1$, were centrifuged at 4,000 rpm for 20 min (eppendorf rotor model 5702/R A-4-38) and were resuspended in a solution volume: lactose 25% and Proskauer and Beck's Medium supplemented with glucose and TWEEN 80® (PBGT: 0.5 g asparagine; 5.0 g monopotassium phosphate; 1.5 g magnesium citrate; 0.5 g sulfate of potassium; 0.5 ml TWEEN 80® and 10.0 g glucose per liter of distilled water). Finally, 1 ml aliquots were lyophilized with $10^4$ bacteria and stored at 25° C. Similarly, the strains can be preserved in a PBS solution (137 mM NaCl; 2.7 mM KCl; 4.3 mM $Na_2HPO_4$; 1.47 mM $KH_2PO_4$, pH 7.4) supplemented with TWEEN 80® 80

0.02% and Glycerol 20% at a final concentration of $10^8$ bacteria per 100 μl. This immunogenic formulation can confer immunity against RSV N protein subtype A and B.

Example VI: Immunogenic Formulation Consisting of $10^9$ Bacteria of the Recombinant Danish BCG Strain for the N Gene of RSV Subtype A The gene is inserted in a copy in the genome of the bacterium under the regulation of the exogenous promoter of phage T7 of constitutive expression in strains of BCG that co-express the polymerase of phage T7. The expression of the protein is cytoplasmic. The immunogenic formulation is in a diluted Sauton SSI solution (125 μg MgSO$_4$, 125 μg K$_2$HPO$_4$, 1 mg L-asparagine, 12.5 μg ferric ammonium citrate, 18.4 mg 85% glycerol, 0.5 mg citric acid in 1 ml of H$_2$O) and was stored at −20° C., or it can be lyophilized and stored at 4° C. Similarly, the strains can be preserved in a PBS solution (137 mM NaCl; 2.7 mM KCl; 4.3 mM Na$_2$HPO$_4$; 1.47 mM KH$_2$PO$_4$, pH 7.4) supplemented with TWEEN 80® 0.02% and Glycerol 20% at a final concentration of $10^9$ bacteria per 100 μl.

The Danish BCG strain was transformed by electrotransformation (24) with the plasmid pMV361$_{PT7}$/N, derived from the plasmid pMV361 (25), which is inserted only once into the genome of the bacterium. This plasmid contains the gene encoding the RSV N protein subtype A, which is expressed under the T7 promoter activated by the expression of phage T7 polymerase (27).

The resulting BCG strain was transformed by electrotransformation (24) with the plasmid pMV261$_{Amp}$/PolT7, derived from pMV261 (25), which resides extrachromosomally in the bacterium in multiple copies. In this plasmid, resistance to the antibiotic kanamycin (27) has been replaced by resistance to the antibiotic hygromycin (Higr). The T7 polymerase of phage T7 is under the control of the constitutive promoter of the BCG hsp60 gene. The resulting recombinant colonies were grown at 37° C. in supplemented Middlebrock 7H9 culture medium until OD$_{600\ nm}$=1, centrifuged at 4000 rpm for 20 min (eppendorf rotor model 5702/R A-4-38) and resuspended in a solution diluted Sauton SSI (125 μg MgSO$_4$, 125 μg K$_2$HPO$_4$, 1 mg L-asparagine, 12.5 μg ferric ammonium citrate, 18.4 mg 85% glycerol, 0.5 mg citric acid in 1 ml of H$_2$O) and was stored at −80° C. This immunogenic formulation can confer immunity against RSV N protein subtype A and B.

Example VII: Protection from RSV BCG-N, Against hMPV Infections

To determine that the vaccines of the invention provide protection against human *Metapneumovirus* (hMPV), mice previously immunized with one of the vaccines of the invention or with a recombinant BCG vaccine for the P protein of hMPV effective against infection by hMPV. These results were compared with mice infected with hMPV without prior immunization and with mice without infection.

The experimental groups, of 3 mice each, are the following:

1) Control Uninfected, unimmunized
2) Infected with hMPV without immunization
3) Immunized with hMPV BCG-P, infected with hMPV
4) Immunized with RSV BCG-N, infected with hMPV First, the infiltrate of polymorphonuclear cells in the lung and bronchoalveolar lavage (BAL) was analyzed by flow cytometry for the 4 groups, determining the percentage of CD11c$^-$/CD11b$^+$/Gr1$^+$ polymorphonuclear cells. The presence of these cells is directly correlated with the inflammatory response to viral infection. FIG. 3-A shows the percentage of CD11c$^-$/CD11b$^+$/Gr1$^+$ cells in BAL for the four groups studied. It is observed that the groups immunized with BCG-P and BCG-N show significantly less inflammatory reaction than the infected group without immunization.

FIG. 3-B shows the percentage of CD11c$^-$/CD11b$^+$/Gr1$^+$ cells in the lung for the four groups studied. As in the previous case, it is observed that the groups immunized with BCG-P and BCG-N show infiltration of inflammatory cells significantly less than that of the infected group without immunization. It can be seen that group 3, immunized with BCG-P, shows a similar result to that of the uninfected group (1).

Second, the viral load in lung tissue of the 4 groups was determined by quantitative PCR (qPCR) (FIG. 4), expressed as the number of copies of the hMPV N protein per 5,000 copies of β-actin. It is observed that the immunized groups have a significantly lower viral load than the unimmunized infected group.

As can be appreciated, the vaccine of the invention provides similar protection against an hMPV infection, to the protection granted by a recombinant BCG vaccine for a protein of the same hMPV virus, in this case, the P protein.

Example VIII: Induction of Humoral Response by BCG RSV-N Vaccine

To determine that the vaccines of the invention induce a Th1-type response, BALB/cJ mice aged 6 to 8 weeks received a subcutaneous injection in the back with 1×10$^8$ CFU of BCG WT or recombinant BCG that expresses the RSV-N protein, in a final volume 100 μL per dose. After 14 days, they were given a booster with the same starting dose. After 21 days from the first injection of BCG WT or BCG-N, the animals were challenged, for which RSV A2 strain 13018-8 obtained from a clinical isolate was used. Pre-immune serum samples were obtained (day 0), before viral challenge (day 21), and 14 days after infection. These samples were analyzed by ELISA at a 1/500 dilution. The results show that animals immunized with BCG-N produce anti-RSV antibodies even in stages prior to viral challenge, this production is significantly higher than unimmunized controls and animals immunized with BCG WT. After the challenge with RSV, the levels of specific IgG immunoglobulins against the virus show an even greater increase that is maintained at day 14 post-infection (FIG. 5).

To establish the isotype of the immunoglobulins produced by immunization, the levels of RSV-specific IgG1 and IgG2a isotype antibodies were analyzed by ELISA in the serum of the test animals. From day 7 post-infection, a significantly greater increase in the production of IgG2a isotype antibodies is observed in animals immunized with the BCG RSV-N vaccine of the invention, compared to control animals, which includes animals vaccinated with wild-type BCG, and not immunized. On the other hand, IgG1 isotype anti-RSV immunoglobulins show an increase in animals vaccinated with BCG-N prior to infection, however, the RSV control group and animals vaccinated with BCG WT already manage to match their production towards day 14 after viral challenge (FIG. 6-A, 6-B). The latter is better evidenced in FIG. 6-C, where it is shown that the ratio of anti-RSV immunoglobulins of isotype IgG2a/IgG1 is higher in animals immunized with the BCG RSV-N vaccine of the invention than in the control group only infected with

15

RSV. As we have already pointed out, this relationship is indicative of an immune response polarized towards a Th1 phenotype.

In order to determine if the humoral response induced by vaccination was capable of protecting against RSV infection, after inactivating complement, the RSV-GFP virus was incubated with sera from animals from all experimental groups on day 14 post-infection and prior to viral challenge, and then HEp-2 cells were infected with these mixtures. In FIG. 7, in the epifluorescence microscopy images, a decrease in the expression of RSV-GFP in the cells previously treated with serum from animals immunized with BCG-N in relation to the other treatments is observed. When quantifying plaque-forming units, a significant decrease in this parameter is evidenced, only in the treatment with serum from day 14 post-infection of animals immunized with BCG-N (FIG. 7-B) and when analyzing the expression of RSV-GFP by flow cytometry, the same trend is evidenced (compare FIG. 7-C with 7-B).

Example IX: Production of Anti-hMPV IgG Antibodies in Animals Immunized with RSV BCG-N In order to evaluate the production of specific immunoglobulins against hMPV, serum samples were obtained from BALB/cJ animals challenged with this virus and previously immunized with the vaccine of the invention, recombinant BCG for the RSV N protein (BCG-N) or with a recombinant BCG vaccine for the hMPV P protein (BCG-P). These results were compared to animals infected with hMPV without prior immunization and with an uninfected control (Mock). The serum are compared at 2 different times: previral challenge and day 7 post-infection. The samples were analyzed by ELISA at a 1/1,000 dilution. The results are seen in FIG. 8, where it is shown that the total anti-hMPV IgG immunoglobulins significantly increased in the vaccinated animals compared to the control groups.

It is highly significant that animals immunized with both RSV BCG-N and hMPV BCG-P achieve the same levels of specific antibodies against human *Metapneumovirus*, before and after viral challenge. This means that the vaccines of the invention, which include RSV proteins, provide protection against human *Metapneumovirus*, similar to that obtained by a specific vaccine for that virus based on a recombinant BCG for the P protein of hMPV.

TABLE 1

| Sequence | SEQ ID NO |
|---|---|
| RSV Subtype A Nucleoprotein (N) gene | 1 |
| RSV Subtype A Nucleoprotein (N) protein | 2 |
| RSV Phosphoprotein (P) gene | 3 |
| RSV Phosphoprotein (P) protein | 4 |
| RSV Matrix protein (M) gene | 5 |
| RSV Matrix protein (M) protein | 6 |
| RSV Small hydrophobic protein (SH) gene | 7 |
| RSV Small hydrophobic protein (SH) protein | 8 |
| RSV Glycoprotein (G) gene | 9 |
| RSV Glycoprotein (G) protein | 10 |
| RSV Subtype B Fusion protein (F) gene | 11 |
| RSV Subtype B Fusion protein (F) protein | 12 |
| RSV Subtype A Matrix protein 2-1 (M2-1) (M2 ORF1) gene | 13 |
| RSV Subtype A Matrix protein 2-1 (M2-1) (M2 ORF1) protein | 14 |
| RSV Subtype A Matrix protein 2-2 (M2-1) (M2 ORF2) gene | 15 |
| RSV Subtype A Matrix protein 2-2 (M2-1) (M2 ORF2) gene | 16 |
| RSV Polymerase (L) gene | 17 |
| RSV Polymerase (L) protein | 18 |

16

TABLE 1-continued

| Sequence | SEQ ID NO |
|---|---|
| Promoter hsp60 polynucleotide | 19 |
| Promoter hsp60 polypeptide | 20 |
| Mycobacteriophage L5 recombinase/tyrosine integrase polynucleotide (allowing insertion of pMV361 into the BCG genome) | 21 |
| Mycobacteriophage L5 recombinase/tyrosine integrase polypeptide (allowing insertion of pMV361 into the BCG genome) | 22 |
| Constitutive endogenous promoter of the gene encoding the alpha-antigen protein of BCG | 23 |
| Inducible promoter of the BCG acr gene | 24 |
| Phage T7 exogenous promoter | 25 |
| Phage T7 polymerase gene | 26 |
| Phage T7 polymerase protein | 27 |
| Human metapneumovirus (hMPV) P protein gene | 28 |
| hMPV P protein protein | 29 |
| Aminoglycoside O-phosphotransferase polynucleotide of the APH(3')-1 superfamily (encodes the resistance gene for Kanamycin) | 30 |
| Aminoglycoside O-phosphotransferase polypeptide of the APH(3')-1 superfamily (encodes the resistance gene for Kanamycin) | 31 |
| RSV subtype B protein F (Peptide signal at the N-terminal) | 32 |

REFERENCES

1. Potash, L., A. A. Tytell, B. H. Sweet, R. A. Machlowitz, J. Stokes, Jr., R. E. Weibel, A. F. Woodhour, and M. R. Hilleman. 1966. Respiratory virus vaccines. I. Respiratory syncytial and parainfluenza virus vaccines. *Am Rev Respir Dis* 93:536.
2. Kim, H. W., J. G. Canchola, C. D. Brandt, G. Pyles, R. M. Chanock, K. Jensen, and R. H. Parrott. 1969. Respiratory syncytial virus disease in infants despite prior administration of antigenic inactivated vaccine. *Am J Epidemiol* 89:422.
3. Polack, F. P., M. N. Teng, P. L. Collins, G. A. Prince, M. Exner, H. Regele, D. D. Lirman, R. Rabold, S. J. Hoffman, C. L. Karp, S. R. Kleeberger, M. Wills-Karp, and R. A. Karron. 2002. A role for immune complexes in enhanced respiratory syncytial virus disease. *J Exp Med* 196:859.
4. Srikiatkhachorn, A., and T. J. Braciale. 1997. Virus-specific memory and effector T lymphocytes exhibit different cytokine responses to antigens during experimental murine respiratory syncytial virus infection. *J Virol* 71:678.
5. Munoz, F. M., P. A. Piedra, and W. P. Glezen. 2003. Safety and immunogenicity of respiratory syncytial virus purified fusion protein-2 vaccine in pregnant women. *Vaccine* 21:3465.
6. Jin, H., X. Cheng, H. Z. Zhou, S. Li, and A. Seddiqui. 2000. Respiratory syncytial virus that lacks open reading frame 2 of the M2 gene (M2-2) has altered growth characteristics and is attenuated in rodents. *J Virol* 74:74.
7. Power, U. F., H. Plotnicky-Gilquin, L. Goetsch, T. Champion, A. Beck, J. F. Haeuw, T. N. Nguyen, J. Y. Bonnefoy, and N. Corvaia. 2001. Identification and characterisation of multiple linear B cell protectopes in the respiratory syncytial virus G protein. *Vaccine* 19:2345.
8. Juhasz, K., S. S. Whitehead, P. T. Bui, J. M. Biggs, J. E. Crowe, C. A. Boulanger, P. L. Collins, and B. R. Murphy. 1997. The temperature-sensitive (ts) phenotype of a cold-passaged (cp) live attenuated respiratory syncytial virus vaccine candidate, designated cpts530, results from a single amino acid substitution in the L protein. *J Virol* 71:5814.

9. Whitehead, S. S., A. Bukreyev, M. N. Teng, C. Y. Firestone, M. St Claire, W. R. Elkins, P. L. Collins, and B. R. Murphy. 1999. Recombinant respiratory syncytial virus bearing a deletion of either the NS2 or SH gene is attenuated in chimpanzees. *J Virol* 73:3438.

10. Bukreyev, A., I. M. Belyakov, J. A. Berzofsky, B. R. Murphy, and P. L. Collins. 2001. Granulocyte-macrophage colony-stimulating factor expressed by recombinant respiratory syncytial virus attenuates viral replication and increases the level of pulmonary antigen-presenting cells. *J Virol* 75:12128.

11. Karron, R. A., P. F. Wright, R. B. Belshe, B. Thumar, R. Casey, F. Newman, F. P. Polack, V. B. Randolph, A. Deatly, J. Hackell, W. Gruber, B. R. Murphy, and P. L. Collins. 2005. Identification of a recombinant live attenuated respiratory syncytial virus vaccine candidate that is highly attenuated in infants. *J Infect Dis* 191:1093.

12. Belshe, R. B., F. K. Newman, E. L. Anderson, P. F. Wright, R. A. Karron, S. Tollefson, F. W. Henderson, H. C. Meissner, S. Madhi, D. Roberton, H. Marshall, R. Loh, P. Sly, B. Murphy, J. M. Tatem, V. Randolph, J. Hackell, W. Gruber, and T. F. Tsai. 2004. Evaluation of combined live, attenuated respiratory syncytial virus and parainfluenza 3 virus vaccines in infants and young children. *J Infect Dis* 190:2096.

13. Polack, F. P., and R. A. Karron. 2004. The future of respiratory syncytial virus vaccine development. *Pediatr Infect Dis J* 23:S65.

14. Chen, M., K. F. Hu, B. Rozell, C. Orvell, B. Morein, and P. Liljestrom. 2002. Vaccination with recombinant alphavirus or immune-stimulating complex antigen against respiratory syncytial virus. *J Immunol* 169:3208.

15. Barrios, C., P. Brawand, M. Berney, C. Brandt, P. H. Lambert, and C. A. Siegrist. 1996. Neonatal and early life immune responses to various forms of vaccine antigens qualitatively differ from adult responses: predominance of a Th2-biased pattern which persists after adult boosting. *Eur J Immunol* 26:1489.

16. Barrios, C., C. Brandt, M. Berney, P. H. Lambert, and C. A. Siegrist. 1996. Partial correction of the TH2/TH1 imbalance in neonatal murine responses to vaccine antigens through selective adjuvant effects. *Eur J Immunol* 26:2666.

17. Ridge, J. P., E. J. Fuchs, and P. Matzinger. 1996. Neonatal tolerance revisited: turning on newborn T cells with dendritic cells. *Science* 271:1723.

18. Arnold, H., D. Bumann, M. Felies, B. Gewecke, M. Sorensen, J. E. Gessner, J. Freihorst, B. U. von Specht, and U. Baumann. 2004. Enhanced Immunogenicity in the Murine Airway Mucosa with an Attenuated *Salmonella* Live Vaccine Expressing OprF-OprI from *Pseudomonas aeruginosa. Infect. Immun.* 72:6546.

19. Dhar, N., V. Rao, and A. K. Tyagi. 2003. Skewing of the Th1/Th2 responses in mice due to variation in the level of expression of an antigen in a recombinant BCG system. *Immunol Lett* 88:175.

20. Marchant, A., T. Goetghebuer, M. O. Ota, I. Wolfe, S. J. Ceesay, D. De Groote, T. Corrah, S. Bennett, J. Wheeler, K. Huygen, P. Aaby, K. P. McAdam, and M. J. Newport. 1999. Newborns develop a Th1-type immune response to *Mycobacterium bovis bacillus* Calmette-Guerin vaccination. *J Immunol* 163:2249.

21. Cirillo, J. D., C. K. Stover, B. R. Bloom, W. R. Jacobs, Jr., and R. G. Barletta. 1995. Bacterial vaccine vectors and *bacillus* Calmette-Guerin. *Clin Infect Dis* 20:1001.

22. Fennelly, G. J., J. L. Flynn, V. ter Meulen, U. G. Liebert, and B. R. Bloom. 1995. Recombinant bacille Calmette-Guerin priming against measles. *J Infect Dis* 172:698.

23. 23 Stover, C. K., V. F. de la Cruz, T. R. Fuerst, J. E. Burlein, L. A. Benson, L. T. Bennett, G. P. Bansal, J. F. Young, M. H. Lee, G. F. Hatfull, and et al. 1991. New use of BCG for recombinant vaccines. Nature 351:456.

24. Kumar, D., B. S. Srivastava, and R. Srivastava. 1998. Genetic rearrangements leading to disruption of heterologous gene expression in mycobacteria: an observation with *Escherichia coli* beta-galactosidase in *Mycobacterium smegmatis* and its implication in vaccine development. *Vaccine* 16:1212.

25. Purkayastha, A., L. A. McCue, and K. A. McDonough. 2002. Identification of a *Mycobacterium tuberculosis* putative classical nitroreductase gene whose expression is coregulated with that of the acr aene within macrophages, in standing versus shaking cultures, and under low oxygen conditions. *Infect Immun* 70:1518.

26. Yoon, Y. G., and M. D. Koob. 2005. Transformation of isolated mammalian mitochondria by bacterial conjugation. *Nucleic Acids Res* 33:e139.

27. Ahmed, S. U., M. Okamoto, T. Oshikawa, T. Tano, A. Sasai, S. Kan, T. Hiroshima, H. Ohue, Y. Moriya, Y. Ryoma, M. Saito, and M. Sato. 2004. Anti-tumor effect of an intratumoral administration of dendritic cells in combination with TS-1, an oral fluoropyrimidine anti-cancer drug, and OK-432, a streptococcal immunopotentiator: involvement of toll-like receptor 4. *J Immunother* 27:432.

The invention claimed is:

1. A method of protecting an individual against human *Metapneumovirus* (hMPV) infections, the method comprising administering to the individual an immunogenic formulation consisting of a strain of recombinant *Bacillus* Calmette-Guerin (BCG) at a concentration in a range from $10^4$ to $10^9$ colony forming units (CFU) per dose in a pharmaceutically acceptable saline buffer solution, wherein the recombinant BCG expresses the N protein of respiratory syncytial virus (RSV) or an immunogenic fragment thereof.

2. The method of claim 1, wherein the immunogenic formulation is administered subcutaneously, percutaneously, or subdermally in a pharmaceutically acceptable physiological saline solution.

3. The method of claim 1, wherein a gene encoding the N protein of the RSV or the immunogenic fragment thereof is inserted into the genome of the BCG strain to express the N protein of the RSV or the immunogenic fragment thereof.

4. The method of claim 3, wherein the expression of the N protein of the RSV or the immunogenic fragment thereof is controlled by an endogenous promoter of the BCG strain which is a constitutive promoter.

5. The method of claim 1, wherein the N protein of the RSV or the immunogenic fragment thereof is expressed by the BCG strain in a soluble-cytoplasmic form.

6. The method of claim 1, wherein the N protein of the RSV or the immunogenic fragment thereof is expressed in a cell membrane-bound form.

7. The method of claim 1, wherein the immunogenic formulation is stabilized by freezing, freeze-drying, or dissolving in a saline buffer prior to the administering.

8. A method of inducing a humoral response specific to human *Metapneumovirus* (hMPV) in an animal comprising administering to the animal an immunogenic formulation consisting of a strain of recombinant *Bacillus* Calmette-Guerin (BCG) at a concentration in a range from $10^4$ to $10^9$ colony forming units (CFU) per dose in a pharmaceutically acceptable saline buffer solution, wherein the recombinant BCG expresses the N protein of RSV or an immunogenic fragment thereof.

9. The method of claim 8, wherein the method induces anti-hMPV IgG antibodies.

* * * * *

SEQUENCE LISTING

```
<160> NUMBER OF SEQ ID NOS: 32

<210> SEQ ID NO 1
<211> LENGTH: 1176
<212> TYPE: DNA
<213> ORGANISM: respiratory syncytial virus

<400> SEQUENCE: 1
atggctctta gcaaagtcaa gttgaatgat acactcaaca aagatcaact tctgtcatct          60
agcaaataca ccatccaacg gagcacagga gatagtattg atactcctaa ttatgatgtg         120
cagaaacaca tcaataagtt atgtggcatg ttattaatca cagaagatgc taatcataaa         180
ttcactgggt taataggtat gttatatgct atgtctaggt taggaagaga agacaccata         240
```

-continued

```
aaaatactca gagatgcggg atatcatgta aaagcaaatg gagtagatgt aacaacacat      300
cgtcaagaca tcaatgggaa agaaatgaaa tttgaagtgt taacattggc aagcttaaca      360
actgaaattc aaatcaacat tgagatagaa tctagaaaat cctacaaaaa aatgctaaaa      420
gaaatgggag aggtagctcc agaatacagg catgattctc ctgattgtgg gatgataata      480
ttatgtatag cagcattagt aataaccaaa ttggcagcag gggatagatc tggtcttaca      540
gccgtgatta ggagagctaa taatgtccta aaaaatgaaa tgaaacgtta caaaggctta      600
ctacccaagg atatagccaa cagcttctat gaagtgtttg aaaaacatcc ccactttata      660
gatgtttttg ttcattttgg tatagcacaa tcttccacca gaggtggcag tagagttgaa      720
gggatttttg caggattgtt tatgaatgcc tatggtgcag ggcaagtaat gctacggtgg      780
ggagtcttag caaatcagt taaaaatatt atgttaggac atgctagtgt gcaagcagaa        840
atggaacaag ttgttgaggt ttatgaatat gcccaaaaat tgggtggaga agcaggattc      900
taccatatat tgaacaaccc aaaagcatca ttattatctt tgactcaatt cctcactttt      960
tccagtgtag tattaggcaa tgctgctggc ctaggcataa tgggagagta cagaggtaca      1020
ccgaggaatc aagatctata tgatgcagca aaggcatatg ctgaacaact caaagaaaat      1080
ggtgtgatta actacagtgt attagacttg acagcagaag aactagaggc tatcaaacat      1140
cagcttaatc caaagataa tgatgtagag ctttga                                   1176
```

```
<210> SEQ ID NO 2
<211> LENGTH: 391
<212> TYPE: PRT
<213> ORGANISM: respiratory syncytial virus

<400> SEQUENCE: 2

Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
            85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
            165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
            195                 200                 205
```

```
Phe Tyr Glu Val Phe Glu Lys His Pro His Phe Ile Asp Val Phe Val
    210             215             220
His Phe Gly Ile Ala Gln Ser Ser Thr Arg Gly Gly Ser Arg Val Glu
225             230             235             240
Gly Ile Phe Ala Gly Leu Phe Met Asn Ala Tyr Gly Ala Gly Gln Val
            245             250             255
Met Leu Arg Trp Gly Val Leu Ala Lys Ser Val Lys Asn Ile Met Leu
            260             265             270
Gly His Ala Ser Val Gln Ala Glu Met Glu Gln Val Val Glu Val Tyr
            275             280             285
Glu Tyr Ala Gln Lys Leu Gly Gly Glu Ala Gly Phe Tyr His Ile Leu
    290             295             300
Asn Asn Pro Lys Ala Ser Leu Leu Ser Leu Thr Gln Phe Pro His Phe
305             310             315             320
Ser Ser Val Val Leu Gly Asn Ala Ala Gly Leu Gly Ile Met Gly Glu
            325             330             335
Tyr Arg Gly Thr Pro Arg Asn Gln Asp Leu Tyr Asp Ala Ala Lys Ala
            340             345             350
Tyr Ala Glu Gln Leu Lys Glu Asn Gly Val Ile Asn Tyr Ser Val Leu
            355             360             365
Asp Leu Thr Ala Glu Glu Leu Glu Ala Ile Lys His Gln Leu Asn Pro
    370             375             380
Lys Asp Asn Asp Val Glu Leu
385             390
```

<210> SEQ ID NO 3
<211> LENGTH: 726
<212> TYPE: DNA
<213> ORGANISM: respiratory syncytial virus

<400> SEQUENCE: 3

```
atggaaaagt ttgctcctga attccatgga gaagatgcaa acaacagggc tactaaattc        60
ctagaatcaa taaagggcaa attcacatca cctaaagatc ccaagaaaaa agatagtatc       120
atatctgtca actcaataga tatagaagta accaagagaa gccctataac atcaaattca       180
accattatta acccaacaaa tgagacagat gataatgcag ggaacaagcc caattatcaa       240
agaaaacctc tagtaagttt caagaagac cctataccaa gtgataatcc cttttcaaaa        300
ctatacaaag aaaccataga gacatttgat aacaatgaag aagaatctag ctattcatat       360
gaagaaataa atgatcagac gaacgataat ataactgcaa gattagatag gattgatgaa       420
aaattaagtg aaatactagg aatgcttcac acattagtag tagcaagtgc aggacctaca       480
tctgctaggg atggtataag agatgccatg gttggtttaa gagaagaaat gatagaaaaa        540
atcagaactg aagcattaat gaccaatgac agattagaag ctatggcaag actcaggaat       600
gaggaaagtg aaaagatggc aaaagacaca tcagatgaag tgtctctcaa tccaacatca       660
gagaaattga caacctgtt ggaagggaat gatagtgaca atgatctatc acttgaagat       720
ttctga                                                                   726
```

<210> SEQ ID NO 4
<211> LENGTH: 241
<212> TYPE: PRT
<213> ORGANISM: respiratory syncytial virus

<400> SEQUENCE: 4

-continued

```
Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
    50                  55                  60

Pro Thr Asn Glu Thr Asp Asp Asn Ala Gly Asn Lys Pro Asn Tyr Gln
65                  70                  75                  80

Arg Lys Pro Leu Val Ser Phe Lys Glu Asp Pro Ile Pro Ser Asp Asn
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
            115                 120                 125

Asp Asn Ile Thr Ala Arg Leu Asp Arg Ile Asp Glu Lys Leu Ser Glu
        130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175

Met Ile Glu Lys Ile Arg Thr Glu Ala Leu Met Thr Asn Asp Arg Leu
            180                 185                 190

Glu Ala Met Ala Arg Leu Arg Asn Glu Glu Ser Glu Lys Met Ala Lys
            195                 200                 205

Asp Thr Ser Asp Glu Val Ser Leu Asn Pro Thr Ser Glu Lys Leu Asn
        210                 215                 220

Asn Leu Leu Glu Gly Asn Asp Ser Asp Asn Asp Leu Ser Leu Glu Asp
225                 230                 235                 240

Phe
```

```
<210> SEQ ID NO 5
<211> LENGTH: 771
<212> TYPE: DNA
<213> ORGANISM: respiratory syncytial virus

<400> SEQUENCE: 5
atggaaacat acgtgaacaa gcttcacgaa ggctccacat acacagctgc tgttcaatac      60
aatgtcctag aaaaagacga tgaccctgca tcacttacaa tatgggtgcc catgttccaa     120
tcatctatgc cagcagattt acttataaaa gaactagcta atgtcaacat actagtgaaa     180
caaatatcca cacccaaggg accttcacta agagtcatga taaactcaag aagtgcattg     240
ctagcacaaa tgcccagcaa atttaccata tgtgctaatg tgtccttgga tgaaagaagc     300
aaactggcat atgatgtaac cacaccctgt gaaatcaagg catgtagtct aacatgccta     360
aaatcaaaaa atatgttaac tacagttaaa gatctcacta tgaagacact caaccccaca     420
catgatatta ttgctttatg tgaatttgaa acatagtaa catcaaaaaa agtcataata     480
ccaacatacc taagatccat cagtgtcaga ataaagatc tgaacacact tgaaaatata     540
acaaccactg aattcaaaaa tgccatcaca aatgcaaaaa tcatcccctta ctcaggatta     600 ctattagtca tcacagtgac tgacaacaaa ggagcattca atacataaa gccgcaaagt     660 caattcatag tagatcttgg agcttaccta gaaaaagaaa gtatatatta tgttaccaca     720
```

```
aattggaagc acacagctac acgatttgca atcaaaccca tggaagatta a              771
```

```
<210> SEQ ID NO 6
<211> LENGTH: 256
<212> TYPE: PRT
<213> ORGANISM: respiratory syncytial virus

<400> SEQUENCE: 6

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
                20                  25                  30

Thr Ile Trp Val Pro Met Phe Gln Ser Ser Met Pro Ala Asp Leu Leu
            35                  40                  45

Ile Lys Glu Leu Ala Asn Val Asn Ile Leu Val Lys Gln Ile Ser Thr
        50                  55                  60

Pro Lys Gly Pro Ser Leu Arg Val Met Ile Asn Ser Arg Ser Ala Leu
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
                100                 105                 110

Lys Ala Cys Ser Leu Thr Cys Leu Lys Ser Lys Asn Met Leu Thr Thr
            115                 120                 125

Val Lys Asp Leu Thr Met Lys Thr Leu Asn Pro Thr His Asp Ile Ile
        130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
                180                 185                 190

Lys Ile Ile Pro Tyr Ser Gly Leu Leu Leu Val Ile Thr Val Thr Asp
            195                 200                 205

Asn Lys Gly Ala Phe Lys Tyr Ile Lys Pro Gln Ser Gln Phe Ile Val
        210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255

<210> SEQ ID NO 7
<211> LENGTH: 195
<212> TYPE: DNA
<213> ORGANISM: respiratory syncytial virus

<400> SEQUENCE: 7
atggaaaata catccataac aatagaattc tcaagcaaat tctggcctta ctttacacta       60
atacacatga tcacaacaat aatctctttg ctaatcataa tctccatcat gactgcaata      120
ctaaacaaac tttgtgaata taacgtattc cataacaaaa cctttgagtt accaagagct      180
cgagtcaaca catag                                                       195

<210> SEQ ID NO 8
<211> LENGTH: 64
<212> TYPE: PRT
<213> ORGANISM: respiratory syncytial virus
```

-continued

<400> SEQUENCE: 8

```
Met Glu Asn Thr Ser Ile Thr Ile Glu Phe Ser Ser Lys Phe Trp Pro
1               5                  10                  15

Tyr Phe Thr Leu Ile His Met Ile Thr Thr Ile Ile Ser Leu Leu Ile
            20                  25                  30

Ile Ile Ser Ile Met Thr Ala Ile Leu Asn Lys Leu Cys Glu Tyr Asn
        35                  40                  45

Val Phe His Asn Lys Thr Phe Glu Leu Pro Arg Ala Arg Val Asn Thr
        50                  55                  60
```

<210> SEQ ID NO 9
<211> LENGTH: 897
<212> TYPE: DNA
<213> ORGANISM: respiratory syncytial virus

<400> SEQUENCE: 9

```
atgtccaaaa acaaggacca acgcaccgct aagacactag aaaagacctg ggacactctc      60
aatcatttat tattcatatc atcgggctta tataagttaa atcttaaatc tatagcacaa     120
atcacattat ccattctggc aatgataatc tcaacttcac ttataattac agccatcata     180
ttcatagcct cggcaaacca caaagtcaca ctaacaactg caatcataca agatgcaaca     240
agccagatca agaacacaac cccaacatac ctcactcagg atcctcagct tggaatcagc     300
ttctccaatc tgtctgaaat tacatcacaa accaccacca tactagcttc aacaacacca     360
ggagtcaagt caaacctgca acccacaaca gtcaagacta aaaacacaac aacaacccaa     420
acacaaccca gcaagcccac tacaaaacaa cgccaaaaca aaccaccaaa caaacccaat     480
aatgattttc acttcgaagt gtttaacttt gtaccctgca gcatatgcag caacaatcca     540
acctgctggg ctatctgcaa aagaatacca aacaaaaaac aggaaagaa accaccacc       600 aagcctacaa aaaaccaac cttcaagaca accaaaaaag atctcaaacc tcaaaccact      660
aaaccaaagg aagtacccac caccaagccc acagaagagc caaccatcaa caccaccaaa     720
acaaacatca caactacact gctcaccaac aacaccacag aaatccaaa actcacaagt      780 caaatggaaa ccttccactc aacctcctcc gaaggcaatc taagcccttc tcaagtctcc     840
acaacatccg agcacccatc acaaccctca tctccaccca acacaacacg ccagtag        897
```

<210> SEQ ID NO 10
<211> LENGTH: 298
<212> TYPE: PRT
<213> ORGANISM: respiratory syncytial virus

<400> SEQUENCE: 10

```
Met Ser Lys Asn Lys Asp Gln Arg Thr Ala Lys Thr Leu Glu Lys Thr
1               5                  10                  15

Trp Asp Thr Leu Asn His Leu Leu Phe Ile Ser Ser Gly Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Thr Ala Ile Ile Phe Ile Ala Ser
        50                  55                  60

Ala Asn His Lys Val Thr Leu Thr Thr Ala Ile Ile Gln Asp Ala Thr
65              70                  75                  80

Ser Gln Ile Lys Asn Thr Thr Pro Thr Tyr Leu Thr Gln Asp Pro Gln
                85                  90                  95
```

```
Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
                180                 185                 190

Lys Pro Gly Lys Lys Thr Thr Thr Lys Pro Thr Lys Lys Pro Thr Phe
        195                 200                 205

Lys Thr Thr Lys Lys Asp Leu Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Thr Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295
```

```
<210> SEQ ID NO 11
<211> LENGTH: 1725
<212> TYPE: DNA
<213> ORGANISM: respiratory syncytial virus

<400> SEQUENCE: 11
atggagttgc caatcctcaa agcaaatgca attaccacaa tcctcgctgc agtcacattt      60
tgctttgctt ctagtcaaaa catcactgaa gaattttatc aatcaacatg cagtgcagtt     120
agcaaaggct atcttagtgc tctaagaact ggttggtata ctagtgttat aactatagaa     180
ttaagtaata tcaaggaaaa taagtgtaat ggaacagatg ctaaggtaaa attgataaac     240
caagaattag ataaatataa aaatgctgta acagaattgc agttgctcat gcaaagcaca     300
acagcagcaa acaatcgagc cagaagagaa ctaccaaggt ttatgaatta tacactcaac     360
aataccaaaa aaaccaatgt aacattaagc aagaaaagga aagaagatt tcttggtttt     420 ttgttaggtg ttggatctgc aatcgccagt ggcattgctg tatctaaggt cctgcactta     480
gaaggagaag tgaacaagat caaaagtgct ctactatcca caaacaaggc cgtagtcagc     540
ttatcaaatg gagttagtgt cttaaccagc aaagtgttag acctcaaaaa actatataga     600 gataacaatgt tacctattgt gaataagcaa agctgcagaa tatcaaatat agaaactgtg     660
atagagttcc aacaaaagaa caacagacta ctagagatta ccagggaatt tagtgttaat     720
gcaggtgtaa ctacacctgt aagcacttac atgttaacta atagtgaatt attgtcatta     780
atcaatgata tgcctataac aaatgatcag aaaaagttaa tgtccaacaa tgttcaaata     840
gttagacagc aaagttactc tatcatgtcc ataataaaag aggaagtctt agcatatgta     900
gtacaattac cactatatgg tgtgatagat acaccttgtt ggaaattaca cacatcccct     960
```

-continued

```
ctatgtacaa ccaacacaaa agaagggtca aacatctgtt taacaagaac tgacagagga    1020
tggtactgtg acaatgcagg atcagtatct ttcttcccac aagctgaaac atgtaaagtt    1080
caatcgaatc gagtattttg tgacacaatg aacagtttaa cattaccaag tgaagtaaat    1140
ctctgcaatt ttgacatatt caatcccaaa tatgattgta aaattatgac ttcaaaaaca    1200
gatgtaagca gctccgttat cacatctcta ggagccattg tgtcatgcta tggcaaaact    1260
aaatgtacag catccaataa aaatcgtgga atcataaaga cattttctaa cgggtgtgat    1320
tatgtatcaa ataaaggggt ggacactgtg tctgtaggta acacattata ttatgtaaat    1380
aagcaagaag gcaaaagtct ctatgtaaaa ggtgaaccaa taataaattt ctatgaccca    1440
ttagtattcc cctctgatga atttgatgca tcaatatctc aagtcaatga gaagattaac    1500
cagagtttag catttattcg taaatccgat gaattattac atcatgtaaa tgctggtaaa    1560
tcaaccacaa atatcatgat aactactata attatagtga ttatagtaat attgttatca    1620
ttaattgctg ttggactgct cctatactgt aaggccagaa gcacaccagt cacactaagc    1680
aaggatcaac tgagtggtat aaataatatt gcatttagta actga                    1725
```

```
<210> SEQ ID NO 12
<211> LENGTH: 574
<212> TYPE: PRT
<213> ORGANISM: respiratory syncytial virus

<400> SEQUENCE: 12

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Asn
65                  70                  75                  80

Gln Glu Leu Asp Lys Tyr Lys Asn Ala Val Thr Glu Leu Gln Leu Leu
                85                  90                  95

Met Gln Ser Thr Thr Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

-continued

```
Ala Gly Val Thr Thr Pro Val Ser Thr Tyr Met Leu Thr Asn Ser Glu
              245                 250                 255

Leu Leu Ser Leu Ile Asn Asp Met Pro Ile Thr Asn Asp Gln Lys Lys
              260                 265                 270

Leu Met Ser Asn Asn Val Gln Ile Val Arg Gln Gln Ser Tyr Ser Ile
              275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
              325                 330                 335

Thr Asp Arg Gly Trp Tyr Cys Asp Asn Ala Gly Ser Val Ser Phe Phe
              340                 345                 350

Pro Gln Ala Glu Thr Cys Lys Val Gln Ser Asn Arg Val Phe Cys Asp
              355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
              405                 410                 415

Tyr Gly Lys Thr Lys Cys Thr Ala Ser Asn Lys Asn Arg Gly Ile Ile
              420                 425                 430

Lys Thr Phe Ser Asn Gly Cys Asp Tyr Val Ser Asn Lys Gly Val Asp
              435                 440                 445

Thr Val Ser Val Gly Asn Thr Leu Tyr Tyr Val Asn Lys Gln Glu Gly
              450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
              485                 490                 495

Glu Lys Ile Asn Gln Ser Leu Ala Phe Ile Arg Lys Ser Asp Glu Leu
              500                 505                 510

Leu His His Val Asn Ala Gly Lys Ser Thr Thr Asn Ile Met Ile Thr
              515                 520                 525

Thr Ile Ile Ile Val Ile Ile Val Ile Leu Leu Ser Leu Ile Ala Val
              530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
              565                 570
```

<210> SEQ ID NO 13
<211> LENGTH: 585
<212> TYPE: DNA
<213> ORGANISM: respiratory syncytial virus

<400> SEQUENCE: 13

```
atgtcacgaa ggaatccttg caaatttgaa attcgaggtc attgcttgaa tggtaagaga       60
tgtcatttta gtcataatta tttttgaatgg ccaccccatg cactgctcgt aagacaaaac      120
tttatgttaa acagaatact taagtctatg gataaaagta tagataccttt atcagaaata     180 agtggagctg cagagttgga cagaacagaa gagtatgctc ttggtgtagt tggagtgcta      240
```

```
gagagttata taggatcaat aaataatata actaaacaat cagcatgtgt tgccatgagc      300
aaactcctca ctgaactcaa tagtgatgat atcaaaaaac tgagagacaa tgaagagcta      360
aattcaccca agataagagt gtacaatact gtcatatcat atattgaaag caacaggaaa      420
aacaataaac aaactatcca tctgttaaaa agattgccag cagacgtatt gaagaaaacc      480
atcaaaaaca cattggatat ccacaagagc ataaccatca caacccaaa agaattaact       540 gttagtgata caaatgacca tgccaaaaat aatgatacta cctga                      585

<210> SEQ ID NO 14
<211> LENGTH: 194
<212> TYPE: PRT
<213> ORGANISM: respiratory syncytial virus

<400> SEQUENCE: 14

Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
                20                  25                  30

His Ala Leu Leu Val Arg Gln Asn Phe Met Leu Asn Arg Ile Leu Lys
        35                  40                  45

Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Leu Thr Val Ser Asp Thr Asn Asp His Ala Lys Asn Asn Asp
            180                 185                 190

Thr Thr

<210> SEQ ID NO 15
<211> LENGTH: 273
<212> TYPE: DNA
<213> ORGANISM: respiratory syncytial virus

<400> SEQUENCE: 15
atgaccatgc aaaaataat gatactacct gacaaatatc cttgtagtat aacttccata       60
ctaataacaa gtagatgtag agtcactatg tataatcgaa agaacacact atatttcaat      120
caaaacaacc caataaccta tgtactca ccgaatcaaa cattcaatga aatccattgg        180
acctcacaag acttgattga cacaattcaa aattttctac agcatctagg tgttattgag      240
gatatatata caatatatat attagtgtca taa                                   273

<210> SEQ ID NO 16
<211> LENGTH: 90
```

-continued

```
<212> TYPE: PRT
<213> ORGANISM: respiratory syncytial virus

<400> SEQUENCE: 16

Met Thr Met Pro Lys Ile Met Ile Leu Pro Asp Lys Tyr Pro Cys Ser
1               5                   10                  15

Ile Thr Ser Ile Leu Ile Thr Ser Arg Cys Arg Val Thr Met Tyr Asn
            20                  25                  30

Arg Lys Asn Thr Leu Tyr Phe Asn Gln Asn Asn Pro Asn Asn His Met
        35                  40                  45

Tyr Ser Pro Asn Gln Thr Phe Asn Glu Ile His Trp Thr Ser Gln Asp
    50                  55                  60

Leu Ile Asp Thr Ile Gln Asn Phe Leu Gln His Leu Gly Val Ile Glu
65                  70                  75                  80

Asp Ile Tyr Thr Ile Tyr Ile Leu Val Ser
                85                  90

<210> SEQ ID NO 17
<211> LENGTH: 6498
<212> TYPE: DNA
<213> ORGANISM: respiratory syncytial virus

<400> SEQUENCE: 17
atggatccca ttattaatgg aaattctgct aatgtttatc taaccgatag ttatttaaaa      60
ggtgttatct ctttctcaga gtgtaatgct ttaggaagtt acatattcaa tggtccttat     120
ctcaaaaatg attataccaa cttaattagt agacaaaatc cattaataga acacatgaat     180
ctaaagaaac taaatataac acagtcctta atatctaagt atcataaagg tgaaataaaa     240
ttagaagagc ctacttattt tcagtcatta cttatgacat acaagagtat gacctcgttg     300
gaacagattg ctaccactaa tttacttaaa aagataataa gaagagctat agaaataagt     360
gatgtcaaag tctatgctat attgaataaa ctagggctta agaaaaggga caagattaaa     420
tccaacaatg acaggatga agacaactca gttattacga ccataatcaa agatgatata      480
ctttcagctg ttaaggataa tcaatctcat cttaaagcag acaaaaatca ctctacaaaa     540
caaaaagaca caatcaaaac aacactcttg aagaaattaa tgtgttcaat gcagcatcct     600
ccatcatggt taatacattg gtttaattta tacacaaaat taaacaacat attaacacag     660
tatcgatcaa atgaggttaa aaaccatggg tttatattga tagataatca aactcttagt     720
ggatttcaat ttattttgaa tcaatatggt tgtatagttt atcataagga actcaaaaga     780
attactgtga caacctataa tcaattcttg acatggaaag atattagcct tagtagatta     840
aatgtttgtt taattacatg gattagtaac tgcttgaaca cattaaataa aagcttaggc     900
ttaagatgcg gattcaataa tgttatcttg acacaactat cctttatggg tgattgtata     960
ctaaagctat ttcacaatga ggggttctac ataataaaag aggtagaggg atttattatg    1020
tctctaattt taaatataac agaagaagat caattcagaa aacgatttta taatagtatg    1080
ctcaacaaca tcacagatgc tgctaataaa gctcagaaaa atctgctatc aagagtatgt    1140
catacattat agataagac agtatccgat aatataataa atggcagatg gataattcta    1200
ttaagtaagt tccttaaatt aattaagctt gcaggtgaca taaaccttaa caatctgagt    1260
gaactatatt ttttgttcag aatatttgga cacccaatgg tagatgaaag acaagccatg    1320
gatgctgtta agttaattg caatgagacc aaatttttact tgttaagcag tttgagtatg    1380
ttaagaggtg cctttatata tagaattata aaagggtttg taaataatta caacagatgg    1440
```

-continued

```
cctactttaa gaaatgctat tgttttaccc ttaagatggt taacttacta taaactaaac    1500
acttatcctt ctttgttgga acttacagaa agagatttga ttgtgttatc aggactacgt    1560
ttctatcgtg agtttcggtt gcctaaaaaa gtggatcttg aaatgattat aaatgataaa    1620
gctatatcac cccctaaaaa tttgatatgg actagtttcc ctagaaatta tatgccgtca    1680
cacatacaaa actatataga acatgaaaaa ttaaaatttt ccgagagtga taaatcaaga    1740
agagtattag agtattattt aagagataac aaattcaatg aatgtgattt atacaactgt    1800
gtagttaatc aaagttatct caacaaccct aatcatgtgg tatcattgac aggcaaagaa    1860
agagaactca gtgtaggtag aatgtttgca atgcaaccgg gaatgttcag acaggttcaa    1920
atattggcag agaaaatgat agctgaaaac attttacaat tctttcctga aagtcttaca    1980
agatatggtg atctagaact acaaaaaata ttagaattga aagcaggaat aagtaacaaa    2040
tcaaatcgct acaatgataa ttacaacaat tacattagta agtgctctat catcacagat    2100
ctcagcaaat tcaatcaagc atttcgatat gaaacgtcat gtatttgtag tgatgtgctg    2160
gatgaactgc atggtgtaca atctctattt tcctggttac atttaactat tcctcatgtc    2220
acaataatat gcacatatag gcatgcaccc ccctatataa gagatcatat tgtagatctt    2280
aacaatgtag atgaacaaag tggattatat agatatcaca tgggtggtat tgaagggtgg    2340
tgtcaaaaac tatggaccat agaagctata tcactattgg atctaatatc tctcaaaggg    2400
aaattctcaa ttactgcttt aattaatggt gacaatcaat caatagatat aagcaaacca    2460
gtcagactca tggaaggtca aactcatgct caagcagatt atttgctagc attaaatagc    2520
cttaaattac tgtataaaga gtatgcaggc ataggtcaca aattaaaagg aactgagact    2580
tatatatcac gagatatgca atttatgagt aaaacaattc aacataacgg tgtatattac    2640
cctgctagta taaagaaagt cctaagagtg ggaccgtgga taaacactat acttgatgat    2700
ttcaaagtga gtctagaatc tataggtagt ttgacacaag aattagaata tagaggtgaa    2760
agtctattat gcagtttaat atttagaaat gtatggttat ataatcaaat tgctctacaa    2820
ttaaaaaatc atgcgttatg taacaataaa ttatatttgg acatattaaa ggttctgaaa    2880
cacttaaaaa cctttttaa tcttgataat attgatacag cattaacatt gtatatgaat    2940
ttacccatgt tatttggtgg tggtgatccc aacttgttat atcgaagttt ctatagaaga    3000
actcctgatt tcctcacaga ggctatagtt cactctgtgt tcatacttag ttattataca    3060
aaccatgact taaaagataa acttcaagat ttgtcagatg atagattgaa taagttctta    3120
acatgcataa tcacgtttga caaaaaccct aatgctgaat tcgtaacatt gatgagagat    3180
cctcaagctt tagggtctga gagacaagct aaaattacta gtgaaatcaa tagactggca    3240
gttacagagg ttttgagtac agctccaaac aaaatattct ccaaaagtgc acaacattat    3300
accactacag agatagatct aaatgatatt atgcaaaata tagaacctac atatcctcac    3360
gggctaagag ttgtttatga aagtttaccc ttttataaag cagagaaaat agtaaatctt    3420
atatcaggta caaaatctat aactaacata ctggaaaaga cttctgccat agacttaaca    3480
gatattgata gagccactga gatgatgagg aaaaacataa ctttgcttat aaggatactt    3540
ccattggatt gtaacagaga taaaagagaa atattgagta tggaaaacct aagtattact    3600
gaattaagca aatatgttag ggaaagatct tggtctttat ccaatatagt tggtgttaca    3660
tcacccagta tcatgtatac aatggacatc aaatatacaa caagcactat agctagtggc    3720
ataattatag agaaatataa tgttaacagt ttaacacgtg gtgagagagg accaactaaa    3780
ccatgggttg gttcatctac acaagagaaa aaaacaatgc cagtttataa tagacaagtt    3840
```

-continued

```
ttaaccaaaa aacaaagaga tcaaatagat ctattagcaa aattggattg ggtgtatgca      3900
tctatagata acaaggatga attcatggaa gaactcagca taggaaccct tgggttaaca      3960
tatgaaaagg ccaaaaaatt atttccacaa tatttaagtg tcaactattt gcatcgcctt      4020
acagtcagta gtagaccatg tgaattccct gcatcaatac cagcttatag aacaacaaat      4080
tatcactttg acactagccc tattaatcgc atattaacag aaaagtatgg tgatgaagat      4140
attgacatag tattccaaaa ctgtataagc tttggcctta gcttaatgtc agtagtagaa      4200
caatttacta atgtatgtcc taacagaatt attctcatac ctaagcttaa tgagatacat      4260
ttgatgaaac ctcccatatt cacaggtgat gttgatattc acaagttaaa acaagtgata      4320
caaaaacagc atatgttttt accagacaaa ataagtttga ctcaatatgt ggaattattc      4380
ttaagtaaca aaacactcaa atctggatct catgttaatt ctaatttaat attggcacat      4440
aaaatatctg actattttca taatacttac attttaagta ctaatttagc tggacattgg      4500
attctaatta tacaacttat gaaagattct aaaggtattt ttgaaaaaga ttggggagag      4560
ggatatataa ctgatcatat gtttattaat ttgaaagttt tcttcaatgc ttataagacc      4620
tatctcttgt gttttcataa aggttatggc aaagcaaaac tggagtgtga tatgaacact      4680
tcagatcttc tatgtgtatt ggaattaata gacagtagtt attggaagtc tatgtctaag      4740 gtattttag aacaaaaagt tatcaaatac attcttagcc aagatgcaag tttacataga      4800
gtaaaaggat gtcatagctt caaattatgg tttcttaaac gtcttaatgt agcagaattt      4860
acagtttgcc cttgggttgt taacatagat tatcatccaa cacatatgaa agcaatatta      4920
acttatatag atcttgttag aatgggattg ataaatatag atagaataca cattaaaaat      4980
aaacacaaat tcaatgatga attttatact tctaatctct tttacattaa ttataacttc      5040
tcagataata ctcatctatt aactaaacat ataaggattg ctaattcaga attagaaaat      5100
aattacaaca aattatatca tcctacacca gaaaccctag agaatatact agccaatccg      5160
attaaaagta atgacaaaaa gacactgaac gactattgta taggtaaaaa tgttgactca      5220
ataatgttac cattgttatc taataagaag cttgttaaat cgtctgcaat gattagaacc      5280
aattacagca aacaagacct gtacaatcta ttccctacgg ttgtgatcga tagaattata      5340
gatcattcag gtaatacagc caaatccaac caactttaca ctactacttc ccatcaaata      5400
tctttagtgc acaatagcac atcactttat tgcatgcttc cttggcatca tattaataga      5460
ttcaattttg tatttagttc tacaggttgt aaaattagta tagagtatat tttaaaagac      5520
cttaaaatta aagatcctaa ttgtatagca ttcataggtg aaggagcagg gaatttatta      5580
ttgcgtacag tggtggaact tcatcctgac ataagatata tttacagaag tctgaaagat      5640
tgcaatgatc atagtttacc tattgagttt ttaaggctat acaatggaca tatcaacatt      5700
gattatggtg aaaatttgac cattcctgct acagatgcaa ccaacaacat tcattggtct      5760
tatttacata taaagtttgc tgaacctatc agtcttttg tatgtgatgc cgaattgcct      5820
gtaacagtca actggagtaa aattataata gaatggagca agcatgtaag aaaatgcaag      5880
tactgttcct cagttaataa atgtacgtta atagtaaaat atcatgctca agatgatatt      5940
gatttcaaat tagacaatat aactatatta aaaacttatg tatgcttagg cagtaagtta      6000
aagggatcgg aggtttactt agtccttaca ataggtcctg caaatatatt tccagtattt      6060
aatgtagtac aaaatgctaa attgatacta tcaagaacca aaaatttcat catgcctaag      6120
aaagctgata aagagtctat tgatgcaaat attaaaagtt tgataccctt tctttgttac      6180
```

```
cctataacaa aaaaaggaat taatactgca ttgtcaaaac taaagagtgt tgttagtgga    6240
gatatactat catattctat agctggacgg aatgaagttt tcagcaataa acttataaat    6300
cataagcata tgaacatctt aaagtggttc aatcatgttt taaatttcag atcaacagaa    6360
ctaaactata accatttata tatggtagaa tctacatatc cttacctaag tgaattgtta    6420
aacagcttga caactaatga acttaaaaaa ctgattaaaa tcacaggtag tctgttatac    6480
aactttcata atgaataa                                                 6498
```

<210> SEQ ID NO 18
<211> LENGTH: 2165
<212> TYPE: PRT
<213> ORGANISM: respiratory syncytial virus

<400> SEQUENCE: 18

```
Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Leu Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
            115                 120                 125

Asn Lys Leu Gly Leu Lys Glu Lys Asp Lys Ile Lys Ser Asn Asn Gly
        130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
            195                 200                 205

Asn Leu Tyr Thr Lys Leu Asn Asn Ile Leu Thr Gln Tyr Arg Ser Asn
        210                 215                 220

Glu Val Lys Asn His Gly Phe Ile Leu Ile Asp Asn Gln Thr Leu Ser
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
            275                 280                 285

Ser Asn Cys Leu Asn Thr Leu Asn Lys Ser Leu Gly Leu Arg Cys Gly
        290                 295                 300

Phe Asn Asn Val Ile Leu Thr Gln Leu Phe Leu Tyr Gly Asp Cys Ile
305                 310                 315                 320
```

-continued

```
Leu Lys Leu Phe His Asn Glu Gly Phe Tyr Ile Ile Lys Glu Val Glu
            325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
            355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
                420                 425                 430

Met Val Asp Glu Arg Gln Ala Met Asp Ala Val Lys Val Asn Cys Asn
            435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
            515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
    595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
            675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735
```

-continued

```
Ile Pro His Val Thr Ile Ile Cys Thr Tyr Arg His Ala Pro Pro Tyr
        740                 745                 750

Ile Arg Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
        770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Val Arg Leu Met Glu Gly Gln Thr His Ala Gln Ala
                820                 825                 830

Asp Tyr Leu Leu Ala Leu Asn Ser Leu Lys Leu Leu Tyr Lys Glu Tyr
                835                 840                 845

Ala Gly Ile Gly His Lys Leu Lys Gly Thr Glu Thr Tyr Ile Ser Arg
        850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
                900                 905                 910

Gln Glu Leu Glu Tyr Arg Gly Glu Ser Leu Leu Cys Ser Leu Ile Phe
                915                 920                 925

Arg Asn Val Trp Leu Tyr Asn Gln Ile Ala Leu Gln Leu Lys Asn His
        930                 935                 940

Ala Leu Cys Asn Asn Lys Leu Tyr Leu Asp Ile Leu Lys Val Leu Lys
945                 950                 955                 960

His Leu Lys Thr Phe Phe Asn Leu Asp Asn Ile Asp Thr Ala Leu Thr
                965                 970                 975

Leu Tyr Met Asn Leu Pro Met Leu Phe Gly Gly Gly Asp Pro Asn Leu
                980                 985                 990

Leu Tyr Arg Ser Phe Tyr Arg Arg Thr Pro Asp Phe Leu Thr Glu Ala
        995                 1000                1005

Ile Val His Ser Val Phe Ile Leu Ser Tyr Tyr Thr Asn His Asp
    1010                1015                1020

Leu Lys Asp Lys Leu Gln Asp Leu Ser Asp Asp Arg Leu Asn Lys
    1025                1030                1035

Phe Leu Thr Cys Ile Ile Thr Phe Asp Lys Asn Pro Asn Ala Glu
    1040                1045                1050

Phe Val Thr Leu Met Arg Asp Pro Gln Ala Leu Gly Ser Glu Arg
    1055                1060                1065

Gln Ala Lys Ile Thr Ser Glu Ile Asn Arg Leu Ala Val Thr Glu
    1070                1075                1080

Val Leu Ser Thr Ala Pro Asn Lys Ile Phe Ser Lys Ser Ala Gln
    1085                1090                1095

His Tyr Thr Thr Thr Glu Ile Asp Leu Asn Asp Ile Met Gln Asn
    1100                1105                1110

Ile Glu Pro Thr Tyr Pro His Gly Leu Arg Val Val Tyr Glu Ser
    1115                1120                1125

Leu Pro Phe Tyr Lys Ala Glu Lys Ile Val Asn Leu Ile Ser Gly
    1130                1135                1140

Thr Lys Ser Ile Thr Asn Ile Leu Glu Lys Thr Ser Ala Ile Asp
```

-continued

```
        1145                1150                1155

Leu Thr  Asp Ile Asp Arg Ala  Thr Glu Met Met Arg  Lys Asn Ile
    1160                1165                1170

Thr Leu  Leu Ile Arg Ile Leu  Pro Leu Asp Cys Asn  Arg Asp Lys
    1175                1180                1185

Arg Glu  Ile Leu Ser Met Glu  Asn Leu Ser Ile Thr  Glu Leu Ser
    1190                1195                1200

Lys Tyr  Val Arg Glu Arg Ser  Trp Ser Leu Ser Asn  Ile Val Gly
    1205                1210                1215

Val Thr  Ser Pro Ser Ile Met  Tyr Thr Met Asp Ile  Lys Tyr Thr
    1220                1225                1230

Thr Ser  Thr Ile Ala Ser Gly  Ile Ile Ile Glu Lys  Tyr Asn Val
    1235                1240                1245

Asn Ser  Leu Thr Arg Gly Glu  Arg Gly Pro Thr Lys  Pro Trp Val
    1250                1255                1260

Gly Ser  Ser Thr Gln Glu Lys  Lys Thr Met Pro Val  Tyr Asn Arg
    1265                1270                1275

Gln Val  Leu Thr Lys Lys Gln  Arg Asp Gln Ile Asp  Leu Leu Ala
    1280                1285                1290

Lys Leu  Asp Trp Val Tyr Ala  Ser Ile Asp Asn Lys  Asp Glu Phe
    1295                1300                1305

Met Glu  Glu Leu Ser Ile Gly  Thr Leu Gly Leu Thr  Tyr Glu Lys
    1310                1315                1320

Ala Lys  Lys Leu Phe Pro Gln  Tyr Leu Ser Val Asn  Tyr Leu His
    1325                1330                1335

Arg Leu  Thr Val Ser Ser Arg  Pro Cys Glu Phe Pro  Ala Ser Ile
    1340                1345                1350

Pro Ala  Tyr Arg Thr Thr Asn  Tyr His Phe Asp Thr  Ser Pro Ile
    1355                1360                1365

Asn Arg  Ile Leu Thr Glu Lys  Tyr Gly Asp Glu Asp  Ile Asp Ile
    1370                1375                1380

Val Phe  Gln Asn Cys Ile Ser  Phe Gly Leu Ser Leu  Met Ser Val
    1385                1390                1395

Val Glu  Gln Phe Thr Asn Val  Cys Pro Asn Arg Ile  Ile Leu Ile
    1400                1405                1410

Pro Lys  Leu Asn Glu Ile His  Leu Met Lys Pro Pro  Ile Phe Thr
    1415                1420                1425

Gly Asp  Val Asp Ile His Lys  Leu Lys Gln Val Ile  Gln Lys Gln
    1430                1435                1440

His Met  Phe Leu Pro Asp Lys  Ile Ser Leu Thr Gln  Tyr Val Glu
    1445                1450                1455

Leu Phe  Leu Ser Asn Lys Thr  Leu Lys Ser Gly Ser  His Val Asn
    1460                1465                1470

Ser Asn  Leu Ile Leu Ala His  Lys Ile Ser Asp Tyr  Phe His Asn
    1475                1480                1485

Thr Tyr  Ile Leu Ser Thr Asn  Leu Ala Gly His Trp  Ile Leu Ile
    1490                1495                1500

Ile Gln  Leu Met Lys Asp Ser  Lys Gly Ile Phe Glu  Lys Asp Trp
    1505                1510                1515

Gly Glu  Gly Tyr Ile Thr Asp  His Met Phe Ile Asn  Leu Lys Val
    1520                1525                1530

Phe Phe  Asn Ala Tyr Lys Thr  Tyr Leu Leu Cys Phe  His Lys Gly
    1535                1540                1545
```

-continued

```
Tyr Gly Lys Ala Lys Leu Glu  Cys Asp Met Asn Thr  Ser Asp Leu
    1550              1555              1560

Leu Cys Val Leu Glu Leu Ile  Asp Ser Ser Tyr Trp  Lys Ser Met
    1565              1570              1575

Ser Lys Val Phe Leu Glu Gln  Lys Val Ile Lys Tyr  Ile Leu Ser
    1580              1585              1590

Gln Asp Ala Ser Leu His Arg  Val Lys Gly Cys His  Ser Phe Lys
    1595              1600              1605

Leu Trp Phe Leu Lys Arg Leu  Asn Val Ala Glu Phe  Thr Val Cys
    1610              1615              1620

Pro Trp Val Val Asn Ile Asp  Tyr His Pro Thr His  Met Lys Ala
    1625              1630              1635

Ile Leu Thr Tyr Ile Asp Leu  Val Arg Met Gly Leu  Ile Asn Ile
    1640              1645              1650

Asp Arg Ile His Ile Lys Asn  Lys His Lys Phe Asn  Asp Glu Phe
    1655              1660              1665

Tyr Thr Ser Asn Leu Phe Tyr  Ile Asn Tyr Asn Phe  Ser Asp Asn
    1670              1675              1680

Thr His Leu Leu Thr Lys His  Ile Arg Ile Ala Asn  Ser Glu Leu
    1685              1690              1695

Glu Asn Asn Tyr Asn Lys Leu  Tyr His Pro Thr Pro  Glu Thr Leu
    1700              1705              1710

Glu Asn Ile Leu Ala Asn Pro  Ile Lys Ser Asn Asp  Lys Lys Thr
    1715              1720              1725

Leu Asn Asp Tyr Cys Ile Gly  Lys Asn Val Asp Ser  Ile Met Leu
    1730              1735              1740

Pro Leu Leu Ser Asn Lys Lys  Leu Val Lys Ser Ser  Ala Met Ile
    1745              1750              1755

Arg Thr Asn Tyr Ser Lys Gln  Asp Leu Tyr Asn Leu  Phe Pro Thr
    1760              1765              1770

Val Val Ile Asp Arg Ile Ile  Asp His Ser Gly Asn  Thr Ala Lys
    1775              1780              1785

Ser Asn Gln Leu Tyr Thr Thr  Thr Ser His Gln Ile  Ser Leu Val
    1790              1795              1800

His Asn Ser Thr Ser Leu Tyr  Cys Met Leu Pro Trp  His His Ile
    1805              1810              1815

Asn Arg Phe Asn Phe Val Phe  Ser Ser Thr Gly Cys  Lys Ile Ser
    1820              1825              1830

Ile Glu Tyr Ile Leu Lys Asp  Leu Lys Ile Lys Asp  Pro Asn Cys
    1835              1840              1845

Ile Ala Phe Ile Gly Glu Gly  Ala Gly Asn Leu Leu  Leu Arg Thr
    1850              1855              1860

Val Val Glu Leu His Pro Asp  Ile Arg Tyr Ile Tyr  Arg Ser Leu
    1865              1870              1875

Lys Asp Cys Asn Asp His Ser  Leu Pro Ile Glu Phe  Leu Arg Leu
    1880              1885              1890

Tyr Asn Gly His Ile Asn Ile  Asp Tyr Gly Glu Asn  Leu Thr Ile
    1895              1900              1905

Pro Ala Thr Asp Ala Thr Asn  Asn Ile His Trp Ser  Tyr Leu His
    1910              1915              1920

Ile Lys Phe Ala Glu Pro Ile  Ser Leu Phe Val Cys  Asp Ala Glu
    1925              1930              1935
```

-continued

```
Leu Pro  Val Thr Val Asn Trp  Ser Lys Ile Ile Ile  Glu Trp Ser
    1940                 1945             1950

Lys His  Val Arg Lys Cys Lys  Tyr Cys Ser Ser Val  Asn Lys Cys
    1955             1960             1965

Thr Leu  Ile Val Lys Tyr His  Ala Gln Asp Asp Ile  Asp Phe Lys
    1970             1975             1980

Leu Asp  Asn Ile Thr Ile Leu  Lys Thr Tyr Val Cys  Leu Gly Ser
    1985             1990             1995

Lys Leu  Lys Gly Ser Glu Val  Tyr Leu Val Leu Thr  Ile Gly Pro
    2000             2005             2010

Ala Asn  Ile Phe Pro Val Phe  Asn Val Val Gln Asn  Ala Lys Leu
    2015             2020             2025

Ile Leu  Ser Arg Thr Lys Asn  Phe Ile Met Pro Lys  Lys Ala Asp
    2030             2035             2040

Lys Glu  Ser Ile Asp Ala Asn  Ile Lys Ser Leu Ile  Pro Phe Leu
    2045             2050             2055

Cys Tyr  Pro Ile Thr Lys Lys  Gly Ile Asn Thr Ala  Leu Ser Lys
    2060             2065             2070

Leu Lys  Ser Val Val Ser Gly  Asp Ile Leu Ser Tyr  Ser Ile Ala
    2075             2080             2085

Gly Arg  Asn Glu Val Phe Ser  Asn Lys Leu Ile Asn  His Lys His
    2090             2095             2100

Met Asn  Ile Leu Lys Trp Phe  Asn His Val Leu Asn  Phe Arg Ser
    2105             2110             2115

Thr Glu  Leu Asn Tyr Asn His  Leu Tyr Met Val Glu  Ser Thr Tyr
    2120             2125             2130

Pro Tyr  Leu Ser Glu Leu Leu  Asn Ser Leu Thr Thr  Asn Glu Leu
    2135             2140             2145

Lys Lys  Leu Ile Lys Ile Thr  Gly Ser Leu Leu Tyr  Asn Phe His
    2150             2155             2160

Asn Glu
    2165

<210> SEQ ID NO 19
<211> LENGTH: 36
<212> TYPE: DNA
<213> ORGANISM: Mycobacterium bovis

<400> SEQUENCE: 19
atggccaaga caattgcgga tccagctgca gaattc                            36

<210> SEQ ID NO 20
<211> LENGTH: 12
<212> TYPE: PRT
<213> ORGANISM: Mycobacterium bovis

<400> SEQUENCE: 20

Met Ala Lys Thr Ile Ala Asp Pro Ala Ala Glu Phe
1               5                  10

<210> SEQ ID NO 21
<211> LENGTH: 1032
<212> TYPE: DNA
<213> ORGANISM: Mycobacteriophage 15

<400> SEQUENCE: 21
gtgaggtact acgcgctgca gacctacgac aacaagatgg acgccgaagc ctggctcgcg     60
```

-continued

```
ggcgagaagc ggctcatcga gatggagacc tggacccctc cacaggaccg ggcgaagaag      120
gcagccgcca cgcgccatcac gctggaggag tacacccgga agtggctcgt ggagcgcgac      180
ctcgcagacg gcaccaggga tctgtacagc gggcacgcgg agcgccgcat ctacccggtg      240
ctaggtgaag tggcggtcac agagatgacg ccagctctgg tgcgtgcgtg gtgggccggg      300
atgggtagga agcacccgac tgcccgccgg catgcctaca acgtcctccg ggcggtgatg      360
aacacagcgg tcgaggacaa gctgatcgca gagaacccgt gccggatcga gcagaaggca      420
gccgatgagc gcgacgtaga ggcgctgacg cctgaggagc tggacatcgt cgccgctgag      480
atcttcgagc actaccggat cgcggcatac atcctggcgt ggacgagcct ccggttcgga      540
gagctgatcg agcttcgccg caaggacatc gtggacgacg catgacgat gaagctccgg      600 gtgcgccgtg gcgcttcccg cgtggggaac aagatcgtcg ttggcaacgc caagaccgtc      660
cggtcgaagc gtcctgtgac ggttccgcct cacgtcgcgg agatgatccg agcgcacatg      720
aaggaccgta cgaagatgaa caagggcccc gaggcattcc tggtgaccac gacgcagggc      780
aaccggctgt cgaagtccgc gttcaccaag tcgctgaagc gtggctacgc caagatcggt      840
cggccggaac tccgcatcca cgacctccgc gctgtcggcg ctacgttcgc cgctcaggca      900
ggtgcgacga ccaaggagct gatggcccgt ctcggtcaca cgactcctag gatggcgatg      960
aagtaccaga tggcgtctga ggcccgcgac gaggctatcg ctgaggcgat gtccaagctg     1020
gccaagacct cc                                                         1032
```

```
<210> SEQ ID NO 22
<211> LENGTH: 344
<212> TYPE: PRT
<213> ORGANISM: Mycobacteriophage 15

<400> SEQUENCE: 22

Val Arg Tyr Tyr Ala Leu Gln Thr Tyr Asp Asn Lys Met Asp Ala Glu
1               5                   10                  15

Ala Trp Leu Ala Gly Glu Lys Arg Leu Ile Glu Met Glu Thr Trp Thr
            20                  25                  30

Pro Pro Gln Asp Arg Ala Lys Lys Ala Ala Ala Ser Ala Ile Thr Leu
        35                  40                  45

Glu Glu Tyr Thr Arg Lys Trp Leu Val Glu Arg Asp Leu Ala Asp Gly
    50                  55                  60

Thr Arg Asp Leu Tyr Ser Gly His Ala Glu Arg Arg Ile Tyr Pro Val
65                  70                  75                  80

Leu Gly Glu Val Ala Val Thr Glu Met Thr Pro Ala Leu Val Arg Ala
                85                  90                  95

Trp Trp Ala Gly Met Gly Arg Lys His Pro Thr Ala Arg Arg His Ala
            100                 105                 110

Tyr Asn Val Leu Arg Ala Val Met Asn Thr Ala Val Glu Asp Lys Leu
        115                 120                 125

Ile Ala Glu Asn Pro Cys Arg Ile Glu Gln Lys Ala Ala Asp Glu Arg
    130                 135                 140

Asp Val Glu Ala Leu Thr Pro Glu Glu Leu Asp Ile Val Ala Ala Glu
145                 150                 155                 160

Ile Phe Glu His Tyr Arg Ile Ala Ala Tyr Ile Leu Ala Trp Thr Ser
                165                 170                 175

Leu Arg Phe Gly Glu Leu Ile Glu Leu Arg Arg Lys Asp Ile Val Asp
            180                 185                 190

Asp Gly Met Thr Met Lys Leu Arg Val Arg Arg Gly Ala Ser Arg Val
```

```
            195                  200                  205
Gly Asn Lys Ile Val Val Gly Asn Ala Lys Thr Val Arg Ser Lys Arg
    210                  215                  220
Pro Val Thr Val Pro Pro His Val Ala Glu Met Ile Arg Ala His Met
225                  230                  235                  240
Lys Asp Arg Thr Lys Met Asn Lys Gly Pro Glu Ala Phe Leu Val Thr
                245                  250                  255
Thr Thr Gln Gly Asn Arg Leu Ser Lys Ser Ala Phe Thr Lys Ser Leu
                260                  265                  270
Lys Arg Gly Tyr Ala Lys Ile Gly Arg Pro Glu Leu Arg Ile His Asp
                275                  280                  285
Leu Arg Ala Val Gly Ala Thr Phe Ala Ala Gln Ala Gly Ala Thr Thr
    290                  295                  300
Lys Glu Leu Met Ala Arg Leu Gly His Thr Thr Pro Arg Met Ala Met
305                  310                  315                  320
Lys Tyr Gln Met Ala Ser Glu Ala Arg Asp Glu Ala Ile Ala Glu Ala
                325                  330                  335
Met Ser Lys Leu Ala Lys Thr Ser
                340

<210> SEQ ID NO 23
<211> LENGTH: 340
<212> TYPE: DNA
<213> ORGANISM: Mycobacterium bovis

<400> SEQUENCE: 23
acgactttcg cccgaatcga catttggcct ccacacacgg tatgttctgg cccgagcaca        60
cgacgacata caggacaaag gggcacaggt atgacagacg tgagccgaaa gattcgagct       120
tggggacgcc gattgatgat cggcacggca gcggctgtag tccttccggg cctggtgggg       180
cttgccggcg gagcggcaac cgcgggcgcg ttctcccggc cggggctgcc ggtcgagtac       240
ctgcaggtgc cgtcgccgtc gatgggccgc gacatcaagg ttcagttcca gagcggtggg       300
aacaactcac ctgcggttta tctgctcgac ggcctgcgcg                             340

<210> SEQ ID NO 24
<211> LENGTH: 150
<212> TYPE: DNA
<213> ORGANISM: Mycobacterium bovis

<400> SEQUENCE: 24
cttctgaacg gcggttggca gacaacaggg tcaatggtcc ccaagtggat caccgacggg        60
cgcggacaaa tggcccgcgc ttcggggact tctgtcccta gccctggcca cgatgggctg       120
gtcggatcaa aggcatccgt ttccatcgat                                       150

<210> SEQ ID NO 25
<211> LENGTH: 23
<212> TYPE: DNA
<213> ORGANISM: Bacteriophage T7

<400> SEQUENCE: 25
taatacgact cactataggg aga                                               23

<210> SEQ ID NO 26
<211> LENGTH: 2655
<212> TYPE: DNA
<213> ORGANISM: Bacteriophage T7
```

-continued

```
<400> SEQUENCE: 26
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa      540
gcatttatgc aagttgtcga ggctgacatg ctctctaagg tctactcgg tggcgaggcg       600 tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc ctgaggtgta caaagcgatt     960
aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtgtttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga gactggaga gattcttcgc    2160 aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
```

-continued

```
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                      2655
```

```
<210> SEQ ID NO 27
<211> LENGTH: 883
<212> TYPE: PRT
<213> ORGANISM: Bacteriophage T7

<400> SEQUENCE: 27

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Ala Ala Ser Ala Ile Gly Arg Ala
        130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
            165                 170                 175

Val Tyr Lys Lys Ala Phe Met Arg Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
            275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
```

-continued 305                     310                     315                     320

Asn Ile Ala Gln Asn Thr Ala Trp Lys Ile Asn Lys Lys Val Leu Ala
                325                     330                     335

Val Ala Asn Val Ile Thr Lys Trp Lys His Cys Pro Val Glu Asp Ile
                340                     345                     350

Pro Ala Ile Glu Arg Glu Glu Leu Pro Met Lys Pro Glu Asp Ile Asp
                355                     360                     365

Met Asn Pro Glu Ala Leu Thr Ala Trp Lys Arg Ala Ala Ala Ala Val
                370                     375                     380

Tyr Arg Lys Asp Lys Ala Arg Lys Ser Arg Arg Ile Ser Leu Glu Phe
385                     390                     395                     400

Met Leu Glu Gln Ala Asn Lys Phe Ala Asn His Lys Ala Ile Trp Phe
                405                     410                     415

Pro Tyr Asn Met Asp Trp Arg Gly Arg Val Tyr Ala Val Ser Met Phe
                420                     425                     430

Asn Pro Gln Gly Asn Asp Met Thr Lys Gly Leu Leu Thr Leu Ala Lys
                435                     440                     445

Gly Lys Pro Ile Gly Lys Glu Gly Tyr Tyr Trp Leu Lys Ile His Gly
                450                     455                     460

Ala Asn Cys Ala Gly Val Asp Lys Val Pro Phe Pro Glu Arg Ile Lys
465                     470                     475                     480

Phe Ile Glu Glu Asn His Glu Asn Ile Met Ala Cys Ala Lys Ser Pro
                485                     490                     495

Leu Glu Asn Thr Trp Trp Ala Glu Gln Asp Ser Pro Phe Cys Phe Leu
                500                     505                     510

Ala Phe Cys Phe Glu Tyr Ala Gly Val Gln His His Gly Leu Ser Tyr
                515                     520                     525

Asn Cys Ser Leu Pro Leu Ala Phe Asp Gly Ser Cys Ser Gly Ile Gln
                530                     535                     540

His Phe Ser Ala Met Leu Arg Asp Glu Val Gly Gly Arg Ala Val Asn
545                     550                     555                     560

Leu Leu Pro Ser Glu Thr Val Gln Asp Ile Tyr Gly Ile Val Ala Lys
                565                     570                     575

Lys Val Asn Glu Ile Leu Gln Ala Asp Ala Ile Asn Gly Thr Asp Asn
                580                     585                     590

Glu Val Val Thr Val Thr Asp Glu Asn Thr Gly Glu Ile Ser Glu Lys
                595                     600                     605

Val Lys Leu Gly Thr Lys Ala Leu Ala Gly Gln Trp Leu Ala Tyr Gly
                610                     615                     620

Val Thr Arg Ser Val Thr Lys Arg Ser Val Met Thr Leu Ala Tyr Gly
625                     630                     635                     640

Ser Lys Glu Phe Gly Phe Arg Gln Gln Val Leu Glu Asp Thr Ile Gln
                645                     650                     655

Pro Ala Ile Asp Ser Gly Lys Gly Leu Met Phe Thr Gln Pro Asn Gln
                660                     665                     670

Ala Ala Gly Tyr Met Ala Lys Leu Ile Trp Glu Ser Val Ser Val Thr
                675                     680                     685

Val Val Ala Ala Val Glu Ala Met Asn Trp Leu Lys Ser Ala Ala Lys
                690                     695                     700

Leu Leu Ala Ala Glu Val Lys Asp Lys Lys Thr Gly Glu Ile Leu Arg
705                     710                     715                     720

Lys Arg Cys Ala Val His Trp Val Thr Pro Asp Gly Phe Pro Val Trp
                725                     730                     735

-continued

```
Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala
```

```
<210> SEQ ID NO 28
<211> LENGTH: 885
<212> TYPE: DNA
<213> ORGANISM: Human metapneumovirus

<400> SEQUENCE: 28
atgtcattcc ctgaaggaaa agatattctt ttcatgggta atgaagcagc aaaattagca      60
gaagctttcc agaaatcatt aagaaaacca ggtcataaaa gatctcaatc tattatagga     120
gaaaaagtga atactgtatc agaaacattg gaattaccta ctatcagtag acctgcaaaa     180
ccaaccatac cgtcagaacc aaagttagca tggacagata aaggtggggc aaccaaaact     240
gaaataaagc aagcaatcaa agtcatggat cccattgaag aagaagagtc taccgagaag     300
aaggtgctac cctccagtga tgggaaaacc cctgcagaaa agaaactgaa accatcaact     360
aacaccaaaa agaaggtttc atttacacca aatgaaccag ggaaatatac aaagttggaa     420
aaagatgctc tagatttgct ctcagataat gaagaagaag atgcagaatc ttcaatctta     480
acctttgaag aaagagatac ttcatcatta agcattgagg ccagattgga atcaatagag     540
gagaaattaa gcatgatatt agggctatta gaaacactca acattgctac agcaggaccc     600
acagcagcaa gagatgggat cagagatgca atgattggcg taagagagga attaatagca     660
gacataataa aggaagctaa agggaaagca gcagaaatga tggaagagga aatgagtcaa     720
cgatcaaaaa taggaaatgg tagtgtaaaa ttaacagaaa aagcaaaaga gctcaacaaa     780
attgttgaag atgaaagcac aagtggagaa tccgaagaag aagaagaacc aaaagacaca     840
caagacaata gtcaagaaga tgacatttac cagttaatta tgtag                      885
```

```
<210> SEQ ID NO 29
<211> LENGTH: 294
<212> TYPE: PRT
<213> ORGANISM: Human metapneumovirus

<400> SEQUENCE: 29

Met Ser Phe Pro Glu Gly Lys Asp Ile Leu Phe Met Gly Asn Glu Ala
1               5                   10                  15
```

```
Ala Lys Leu Ala Glu Ala Phe Gln Lys Ser Leu Arg Lys Pro Gly His
            20                  25                  30

Lys Arg Ser Gln Ser Ile Ile Gly Glu Lys Val Asn Thr Val Ser Glu
        35                  40                  45

Thr Leu Glu Leu Pro Thr Ile Ser Arg Pro Ala Lys Pro Thr Ile Pro
    50                  55                  60

Ser Glu Pro Lys Leu Ala Trp Thr Asp Lys Gly Gly Ala Thr Lys Thr
65                  70                  75                  80

Glu Ile Lys Gln Ala Ile Lys Val Met Asp Pro Ile Glu Glu Glu Glu
                85                  90                  95

Ser Thr Glu Lys Lys Val Leu Pro Ser Ser Asp Gly Lys Thr Pro Ala
            100                 105                 110

Glu Lys Lys Leu Lys Pro Ser Thr Asn Thr Lys Lys Lys Val Ser Phe
        115                 120                 125

Thr Pro Asn Glu Pro Gly Lys Tyr Thr Lys Leu Glu Lys Asp Ala Leu
    130                 135                 140

Asp Leu Leu Ser Asp Asn Glu Glu Glu Asp Ala Glu Ser Ser Ile Leu
145                 150                 155                 160

Thr Phe Glu Glu Arg Asp Thr Ser Ser Leu Ser Ile Glu Ala Arg Leu
                165                 170                 175

Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Val Arg Glu Glu Leu Ile Ala Asp Ile Ile Lys
    210                 215                 220

Glu Ala Lys Gly Lys Ala Ala Glu Met Met Glu Glu Glu Met Ser Gln
225                 230                 235                 240

Arg Ser Lys Ile Gly Asn Gly Ser Val Lys Leu Thr Glu Lys Ala Lys
                245                 250                 255

Glu Leu Asn Lys Ile Val Glu Asp Glu Ser Thr Ser Gly Glu Ser Glu
            260                 265                 270

Glu Glu Glu Glu Pro Lys Asp Thr Gln Asp Asn Ser Gln Glu Asp Asp
        275                 280                 285

Ile Tyr Gln Leu Ile Met
    290
```

```
<210> SEQ ID NO 30
<211> LENGTH: 816
<212> TYPE: DNA
<213> ORGANISM: Artificial Sequence
<220> FEATURE:
<223> OTHER INFORMATION: Aminoglycoside O-phosphotransferase
      polynucleotide of the APH(3')-1 superfamily (encodes the
      resistance gene for Kanamycin)

<400> SEQUENCE: 30
atgagccata ttcaacggga aacgtcttgc tcgaggccgc gattaaattc caacatggat      60
gctgatttat atgggtataa atgggctcgc gataatgtcg ggcaatcagg tgcgacaatc     120
tatcgcttgt atgggaagcc ccatgcgcca gagttgtttc tgaaacatgg caaaggtagc     180
gttgccaatg atgttacaga tgagatggtc agactaaact ggctgacgga atttatgcct     240
cttccgacca tcaagcattt tatccgtact cctgatgatg catggttact caccactgcg     300
atccccggga aaacagcatt ccaggtatta gaagaatatc ctgattcagg tgaaaatatt     360
gttgatgcgc tggcagtgtt cctgcgccgg ttgcattcga ttcctgtttg taattgtcct     420
```

-continued

```
tttaacagcg atcgcgtatt tcgtctcgct caggcgcaat cacgaatgaa taacggtttg      480
gttgatgcga gtgattttga tgacgagcgt aatggctggc ctgttgaaca agtctggaaa      540
gaaatgcata atcttttgcc attctcaccg gattcagtcg tcactcatgg tgatttctca      600
cttgataacc ttatttttga cgaggggaaa ttaataggtt gtattgatgt tggacgagtc      660
ggaatcgcag accgatacca ggatcttgcc atcctatgga actgcctcgg tgagttttct      720
ccttcattac agaaacggct ttttcaaaaa tatggtattg ataatcctga tatgaataaa      780
ttgcagtttc atttgatgct cgatgagttt ttctaa                                816
```

<210> SEQ ID NO 31

<400> SEQUENCE: 31

000

<210> SEQ ID NO 32
<211> LENGTH: 49
<212> TYPE: PRT
<213> ORGANISM: respiratory syncytial virus

<400> SEQUENCE: 32

```
His Met Lys Lys Arg Gly Leu Thr Val Ala Val Ala Gly Ala Ala Ile
1               5                   10                  15

Leu Val Ala Gly Leu Ser Gly Cys Ser Ser Asn Lys Ser Thr Thr Gly
            20                  25                  30

Ser Gly Glu Thr Thr Thr Thr Ala Ala Gly Thr Thr Ala Ser Pro Gly
        35                  40                  45

Gly
```